(12) United States Patent
Takahashi et al.

(10) Patent No.: US 7,491,868 B2
(45) Date of Patent: Feb. 17, 2009

(54) MANNOSE BINDING LECTIN KNOCK-OUT MICE AND METHODS OF USE THEREOF

(75) Inventors: Kazue Takahashi, Boston, MA (US); R. Alan Ezekowitz, Princeton, NJ (US); Lei Shi, Glen Mills, PA (US)

(73) Assignee: The General Hospital Corporation, Boston, MA (US)

( * ) Notice: Subject to any disclaimer, the term of this patent is extended or adjusted under 35 U.S.C. 154(b) by 10 days.

(21) Appl. No.: 11/568,295

(22) PCT Filed: Apr. 20, 2005

(86) PCT No.: PCT/US2005/013549

§ 371 (c)(1),
(2), (4) Date: Jun. 25, 2007

(87) PCT Pub. No.: WO2006/073432

PCT Pub. Date: Jul. 13, 2006

(65) Prior Publication Data

US 2007/0250939 A1 Oct. 25, 2007

Related U.S. Application Data

(60) Provisional application No. 60/567,109, filed on Apr. 30, 2004.

(51) Int. Cl.
*A01K 67/027* (2006.01)
*A01K 67/00* (2006.01)
*A01K 67/033* (2006.01)
*C12N 15/00* (2006.01)

(52) U.S. Cl. ............................... 800/18; 800/8; 800/25

(58) Field of Classification Search .................. 800/18, 800/8, 25
See application file for complete search history.

(56) References Cited

U.S. PATENT DOCUMENTS

2004/0043034 A1* 3/2004 Jensenius et al. ......... 424/185.1

OTHER PUBLICATIONS

Moreadith et al., Gene targeting in embryonic stem cells: the new physiology and metabolism. J Mol Med. 75(3):208-16, 1997.*
Leonard et al., Role of the common cytokine receptor gamma chain in cytokine signaling and lymphoid development. Immunol Rev. 148:97-114, 1995.*
Griffiths et al., Current concepts of PLP and its role in the nervous system. Microsc Res Tech. 41(5):344-58, 1998.*
Chu et al., Repeated respiratory Mycoplasma pneumoniae infections in mice: effect of host genetic background, Microbes Infect. 8(7):1764-72, 2006.*
Sastry et al., Characterization of murine mannose-binding protein genes Mbl1 and Mbl2 reveals features common to other collectin genes, Mamm Genome. 6(2):103-10, 1995.*

Kuhlman, Marcella, et al. "The human mannose-binding protein functions as an opsonin." Journal of Experimental Medicine, vol. 169. 1989. pp. 1733-1745.
Sastry, Kedarnath, et al. "Molecular Characterization of the Mouse Mannose-Binding Proteins: The mannose-binding protein A but not C is an acute phase reactant." Journal of Immunology, vol. 147, No. 2, 1991. pp. 692-697.
Sheriff, Steven, et al. "Human Mannose-Binding Protein Carbohydrate Recognition Doman Trimerizes Through a Triple Alpha-Helical Coiled Coil." Structural Biology, vol. 1, No. 11. Nature Publishing Group. 1994. pp. 789-794.
Thiel, Steffan, et al. "A Second Serine Protease Associated with Mannan-Binding Lectin That Activates Complement." Nature, vol. 386. Apr. 3, 1997. pp. 506-510.
Dahl, Mads, et al. MASP-3 and its Association with Distinct Complexes of the Mannan-Binding Lectin Complement Activation Pathway. Immunity, vol. 15. Jul. 2001. pp. 127-135.
Liu, H., et al. "Characterization and Quantification of Mouse Mannan-Binding Lection (MBL-A and MBL-C) and Study of Acute Phase Responses." Scandanavian Journal of Immunology, vol. 53. Jan. 19, 2001. pp. 489-497.
Neth, Olaf, et al. "Deficiency of Mannose-Binding Lectin and Burden of Infection in Children with Malignancy: A Prospective Study." The Lancet, vol. 358. Aug. 25, 2001. pp. 614-618.
Peterslund, Niels A., et al. "Associated Between Deficiency of Mannose-Binding Lectin and Severe Infections After Chemotherapy." The Lancet, vol. 358. Aug. 25, 2001. pp. 637-638.
Mulligan, Charles G., et al. "Mannose-Binding Lectin Gene Polumorphisms Are Associated With Major Infection Following Allogenic Hemopoietic Stem Cell Transplantation." Blood, vol. 99, No. 10. May 15, 2002. pp. 3524-3529.
Neth, Olaf, et al. "Enhancement of Complement Activation and Opsonophagosytosis by Complexes of Mannose-Binding Lectin with Mannose-Binding Lectin-Associated Serine Protease After Binding to *Staphylococcus aureus*." Journal of Immunology, vol. 169. 2002. pp. 4430-4436.
Takahashi, Kazue. "Lack of Mannose-Binding Lectin-A Enhances Survival in a Mouse Model of Acute Septic Peritonitis." Microbes and Infection, vol. 4. 2002. pp. 773-784.
Gadjeva, M., et al. "Mannan-Binding Lectin Modulates the Response to HSV-2 Infection." Clin. Exp. Immunology, vol. 138. 2004. pp. 304-311.
Shi, Lei, et al. "Mannose-Binding Lectin-Deficient Mice Are Susceptible to Infection with *Staphylococcus aureus*." Journal of Experimental Medicine, vol. 199, No. 10. Rockefellar University Press. May 17, 2004. pp. 1379-1390.

(Continued)

*Primary Examiner*—Thaian N. Ton
*Assistant Examiner*—Wu-Cheng Winston Shen
(74) *Attorney, Agent, or Firm*—Dann, Dorfman, Herrell & Skillman; Robert C. Netter; Kathleen D. Rigaut

(57) ABSTRACT

A transgenic non-human animal with alterations in the MBL gene is prepared by introduction of a gene encoding an altered MBL protein into a host non-human animal. Methods for using transgenic mice so generated to screen for agents that effect MBL's cellular modulating activity are also provided.

7 Claims, 10 Drawing Sheets

OTHER PUBLICATIONS

Takahashi, Kazue, et al. "Mannose-Binding Lectin Modulates Thymus-Dependent Antigen Responses." Molecular Immunology, vol. 41. 2004. pp. 201-333 (Conference Abstract).

Hart, Melanie L., et al. "Gastrointestinal Ischemia-Reperfusion Injury is Lectin Complement Pathway Dependent Without Involving C1q." Journal of Immunology, vol. 174. pp. 6373-6380.

Moller-Kristensen, M., et al. "Mannan-Binding Lectin Recognizes Structures on Ischaemic Reperfused Mouse Kidneys and is Implicated in Tissue Injury." Scandanavian Journal of Immunology, vol. 61. 2005. pp. 426-434.

Walsh, Mary C., et al. "Mannose-Binding Lectin is a Regulator of Inflammation That Accompanies Myocardial Ischemia and Reperfusion Injury." Journal of Immunology, vol. 175. 2005. pp. 541-546.

McMullen, Megan E., et al. "Mannose-Binding Lectin Binds IgM to Activate the Lectin Complement Pathway In Vitro and In Vivo." Immunobiology, vol. 211. 2006. pp. 759-766.

Moller-Kristensen, Mette, et al. "Deficiency of Mannose-Binding Lectin Greatly Increases Susceptibility to Postburn Infection with Pseudomonas Aeruginosa." Journal of Immunology, vol. 176. 2006. pp. 1769-1775.

Zhang, Ming, et al. "Activation of the Lectin Pathway by Natural IgM in a Model of Ischemia-Reperfusion Injury." Journal of Immunology, vol. 177. 2006. pp. 4727-4734.

Takahashi, "Mannose Binding Protein a Null Mice Display Enhanced Survival in an Acute Septic Peritonitis Model," Soc. Leuk. Biol., 34th Ann. Meeting, MA, Oct. 5-8, 2000.

\* cited by examiner a. Plasma
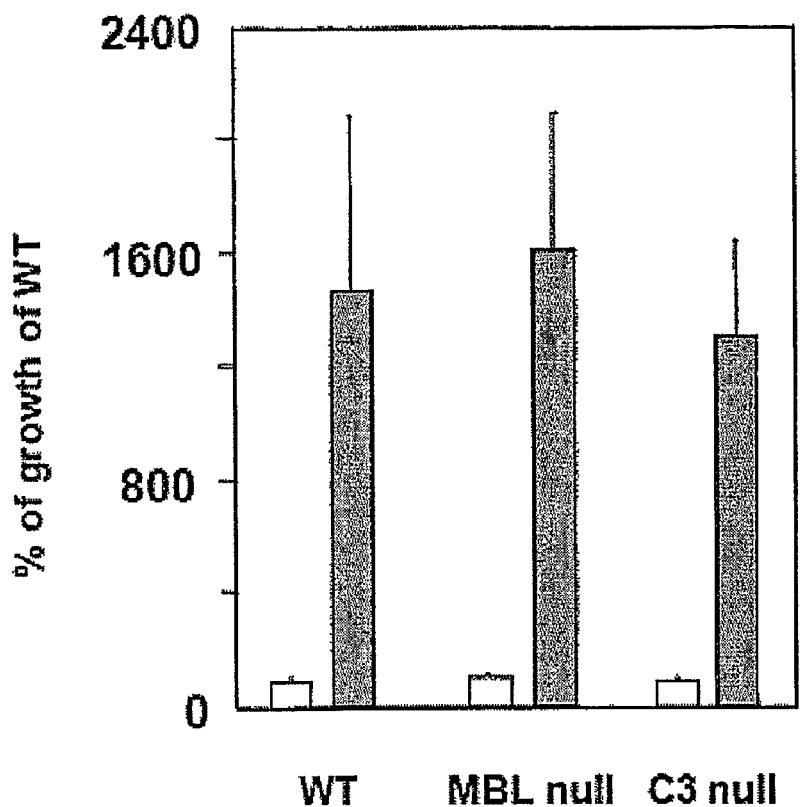
b. Whole Blood
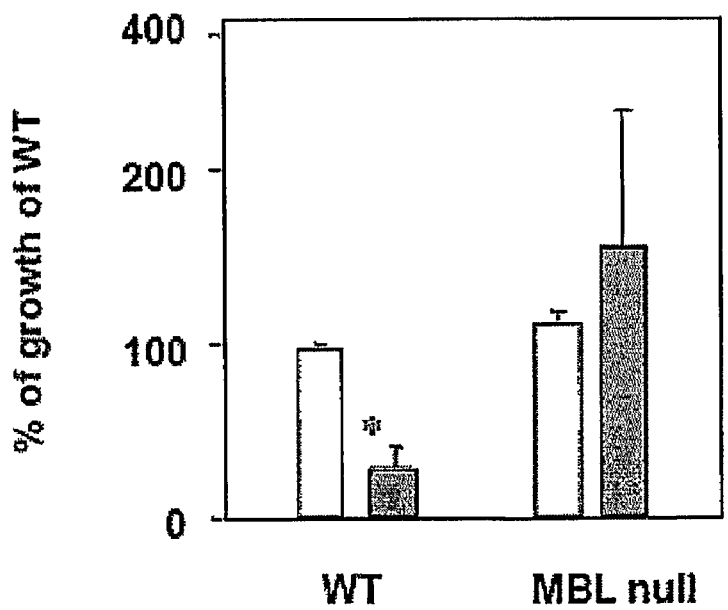
Figure 4

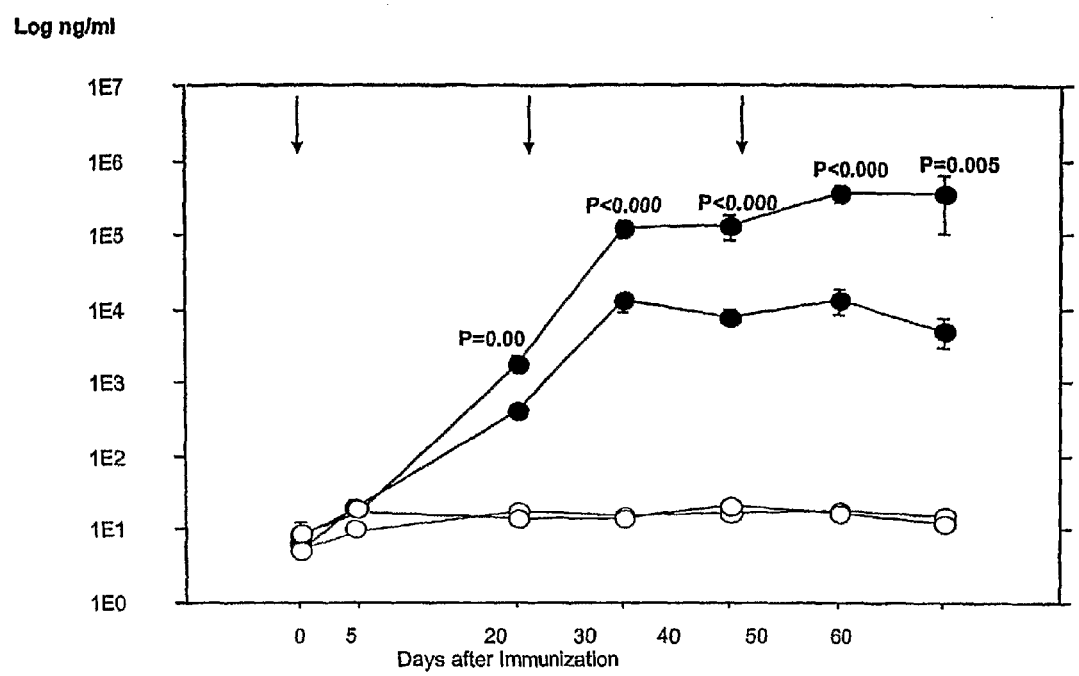
Figure 8: Anti-GBSIII PS IgG Response
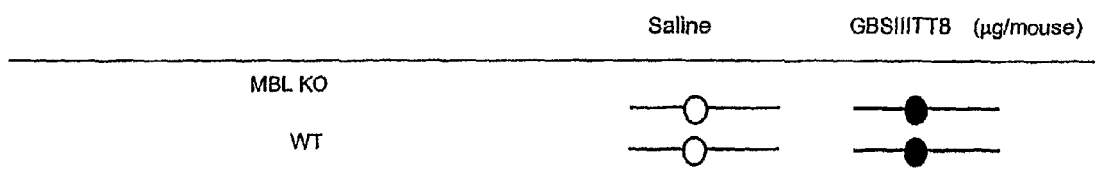

MANNOSE BINDING LECTIN KNOCK-OUT MICE AND METHODS OF USE THEREOF

This application is a 35 U.S.C. §371 application of PCT/US2005/013549 filed 20 Apr. 2005 which in turn claims priority to U.S. provisional application No. 60/567,109 filed 30 Apr. 2004, the disclosure of each of these applications being incorporated by reference herein.

Pursuant to 35 U.S.C. §202(c) it is acknowledged that the U.S. Government has certain rights in the invention described herein, which was made in part with funds from the National Institutes of Health, Grant Number RO1 A142788

FIELD OF THE INVENTION

This invention relates the fields of recombinant DNA technology, transgenic animals and immunology. More specifically, transgenic nonhuman animals are provided which are devoid of all mannose-lectin binding (MBL) activity. Methods of using such animals to assess the role of MLB in the modulation of immune responses are also provided.

BACKGROUND OF THE INVENTION

Several publications are cited in this application by numerals in parentheses in order to more fully describe the state of the art to which this invention pertains. Certain patents are also cited. The disclosure of each of these citations is incorporated by reference herein.

A basic function of innate immunity is restriction of the early proliferation of infectious agents (1, 2). Numerous molecules and effector cells conspire to restrict this initial spread of an infectious focus. Some examples of first line host defense molecules include antimicrobial peptides, natural antibodies, complement proteins, lipopolysaccharide binding protein (LBP), soluble receptors and collectins (3-5). The collectins are multimeric carbohydrate recognition domain-containing molecules with collagen stalks that include the pulmonary surfactant proteins-A and -D, conglutinin, CL-43, CL-46, and the MBL (6-9). MBL appears to be a prototypic pattern recognition molecule that is able to recognize the molecular patterns that decorate a wide range of microorganisms.

Infectious agents that are recognized by MBL include certain Gram positive and Gram negative bacteria, yeast, parasites, mycobacteria, and viruses (7, 10).

MBL was first surmised to play a role in host defense based on its overall structural similarity with the first complement component C1q (11, 12). Next, in vitro observations demonstrated that MBL could bind and opsonize bacteria as well as the yeast cell wall product mannan (13). The idea that a relative lack of MBL might predispose the host to infection was based on the description of an MBL-dependent opsonic defect in human serum that correlated with a phenotype of recurrent infection (14). These patients were found to have one of three amino acid substitution single nucleotide polymorphisms (SNPs) in exon 1 of the MBL gene that disrupt the collagen helix (15). It appears that the disordered collagen chain acts like a dominant negative resulting in a decrease in circulating levels of MBL that can activate complement. More detailed analysis of the MBL gene has revealed seven distinct MBL haplotypes in humans, four of which (LYPB, LYQC, HYPD, and LXPA) dictate low serum levels (16). Interestingly, there is a high rate of haplotype variation in various human populations with a range of heterozygosity from 15% in Caucasians to 30% in certain African populations (17, 18).

Importantly, MBL seems to be able to distinguish species self as well as altered self, e.g. in the form of apoptotic cells from non-self (19). The specificity that allows the distinction of surfaces of virally infected cells and transformed cells from normal host cells depends on both fine recognition of molecular patterns and a macropattern (3). The macropattern appears to be dictated by the spatial orientation of the carbohydrate binding domains and the differences in geometry of the sugars that adorn microorganisms versus host glycoproteins (3, 20, 21). MBL is able to activate complement via a novel mechanism that co-opts the mannose-binding lectin associated serine protease (MASP) (22, 23), MASP-2 which then mimics the classical pathway convertase to cleave the third complement component (C3) (23). In this way the MBL complement pathway is activated in an antibody-independent manner. MBL therefore has many functional properties that are reminiscent of an antibody and in fact MBL is considered as an opsonin (24-26).

The initial response to infection is a complex interaction between a variety of pattern recognition molecules that trigger the downstream physiological cascades of clotting, cytokine, and chemokine release and interface with effector cells such as neutrophils (27, 28). Neutrophils express complement receptors, MBL receptors (collectin receptors) (29, 30) and the receptor for LBP (31).

Wright and colleagues linked humoral and cellular interactions and drew attention to the importance of co-operative interactions between neutrophils and opsonins in combating infection (32, 33). More recent examples that have exploited the use of null animals to explore such interactions and are germane to this present study, include the interaction of LBP and neutrophils in resistance to intraperitoneal *Salmonella* infection (34, 35). A similar synergistic interaction between neutrophils and MBL is suggested by clinical observations that chemotherapy-induced neutropenic patients with haplotypes that specify low serum MBL levels (9, 36, 37) appear more susceptible to infection (38). These clinical observations together with in vitro studies suggest that MBL plays a key role as an ante-antibody in first line host defense (39, 40) and support a role for MBL in combating infection in vivo.

SUMMARY OF THE INVENTION

This invention provides non-human transgenic animals in which are devoid of all MBL activity and methods of use thereof. The MLB knockout mice of the invention are fertile and appear to develop normally.

In a preferred embodiment of the invention, the KO mice of the invention are inoculated with microbes, including without limitation, bacteria, fungi, parasites and viruses. The course of infection is then analyzed to identify biochemical and pathological differences between wild type mice and mice devoid of MBL activity. Such mice may also be used to advantage in assays for the identification of therapeutic agents useful for the treatment of the microbial infections being analyzed. In this manner, a variety of anti-fungal, anti-viral and anti-bacterial agents can be identified and analyzed for efficacy.

In accordance with one aspect of the present invention, it has been discovered that MBL knockout mice mount a rapid and robust response to immunization with antigens. Accordingly, such mice provide a superior model system to facilitate the rapid and efficient generation of immuno-specific monoclonal antibodies to selected antigens.

BRIEF DESCRIPTION OF THE DRAWINGS

FIG. 4. Restricted bacterial growth in blood of WT mice but enhanced growth in blood but not in plasma of MBL null mice. Open bars at 10 min and closed bars at 2 h. a, Bacterial growth in plasma. Results are shown as a percentage of bacterial growth in WT plasma at 10 min. Pooled plasma was used and the assay was performed in triplicates as described in the Materials and Methods. Bars indicate mean ±SD. b, Results are shown as a percentage of bacterial growth in WT blood at 10 min. Blood was collected from 4 mice individually and the assay was performed in triplicates as described in the Materials and Methods. Bars indicate mean ±SD. *, P<0.05

FIG. 8. A graph showing the anti-GBSIII PS IgG response in MBL null and wild type mice.

DETAILED DESCRIPTION OF THE INVENTION

Figure 1:
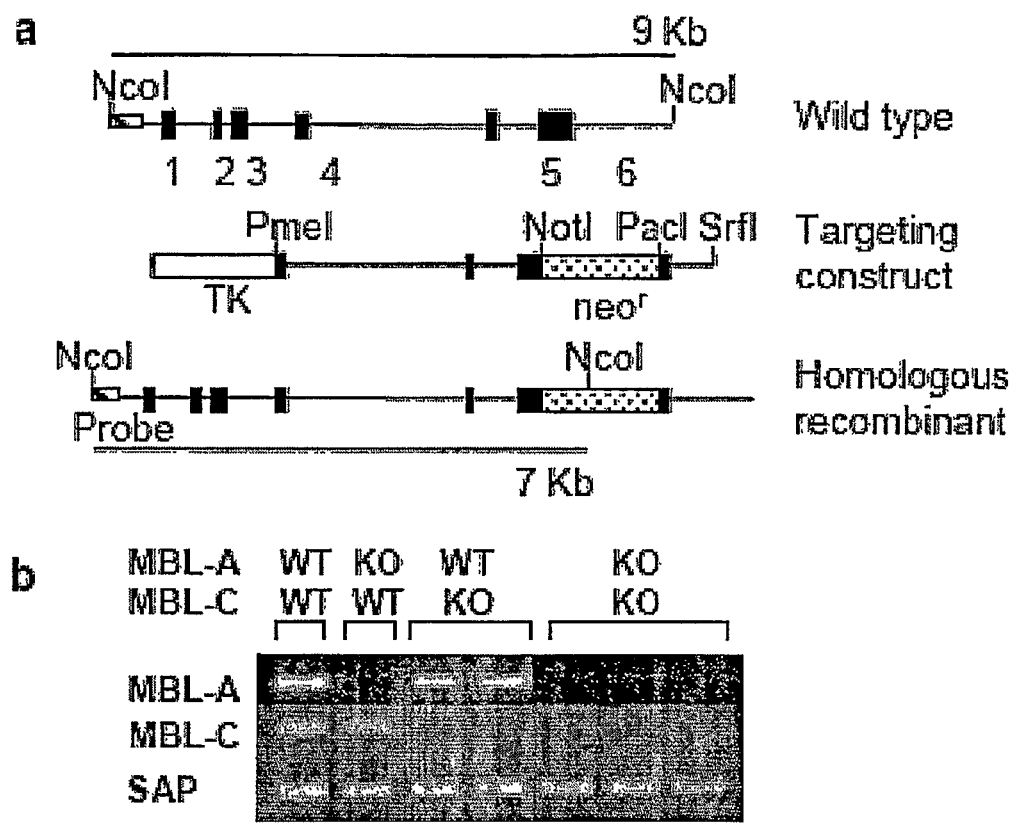
FIG. 1. Generation and characterization of MBL null mice. a, MBL-C targeting construct. Genomic organization of MBL-C is shown and compared with the targeting vector and homologous recombinant. b, RT-PCR analysis of transcript for MBL-A, MBL-C, and serum amyloid protein (SAP) in liver. c, Serum levels of MBL-A and MBL-C in WT, MBL-C KO and MBL null mice. Circles indicate individual mice and bars indicate mean value for each group. d, C4 cleaving activity of serum. The capacity of serum to activate C4 via the MBL complement pathway (left panel) or classical pathway (right panel) was assayed as described above. Circles indicate individual mice and bars indicate the mean value for each group. e, C4 cleaving activity. Comparison of rhMBL with purified MBL-A and MBL-C. Closed circle, rhMBL; open circle, MBL-A; inverted closed triangle, MBL-C.
Figure 1:
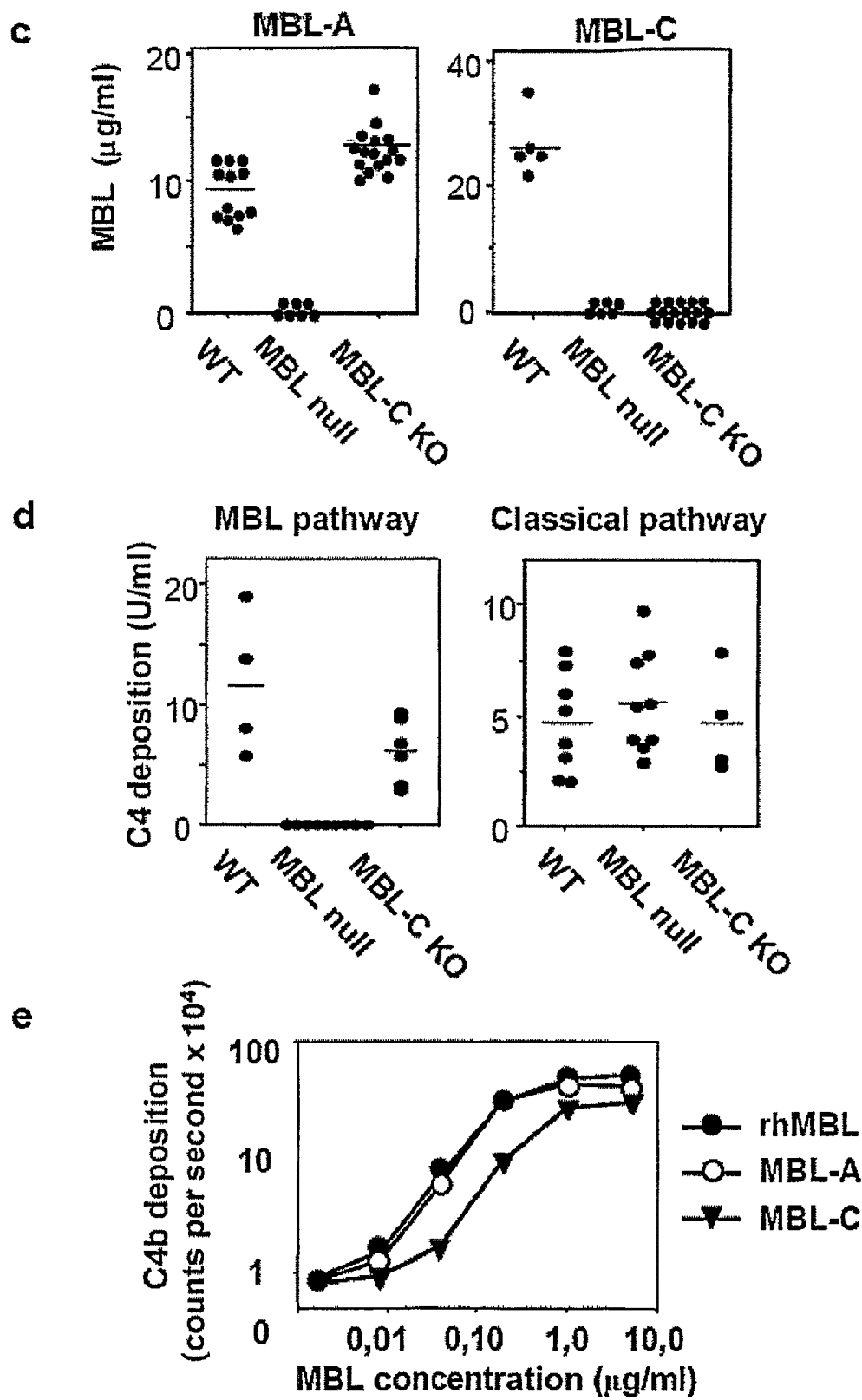

In order to provide formal proof that indeed MBL is important in host defense in vivo, we set out to create a mouse model of MBL deficiency. While humans and new world monkeys have a single MBL gene, two homologous forms of MBL, designated MBL-A and MBL-C, have been identified in rodents (41, 42). MBL-A and MBL-C, the respective gene products of the mb11 and mb12 genes, are 50% homologous (43), have distinct and overlapping binding specificities (43-45), are found predominantly in serum, and are able to bind MASPs to activate complement (46). The relative physiological role of these two proteins in vivo has not been clearly defined (43, 46-49). In accordance with the present invention, MBL-A and MBL-C double KO (MBL null) mice were created. These MBL null mice lack MBL in serum and lack the MBL complement pathway. We chose to infect these mice with $S.$ $aureus$ as this organism is a significant cause of bacteremia in humans world-wide (50, 51). Treatment of $S.$ $aureus$ infections is increasingly problematic with the emergence of widespread antibiotic resistance (52, 53). While there are clinical identifiers that indicate likelihood of complication as a result of $S.$ $aureus$ infection there is a paucity of data that pertains to genetic variation in host factors that confer resistance to $S.$ $aureus$. We found that MBL null mice are highly susceptible to an i.v. inoculation of $S.$ $aureus$ as at 48 h post inoculation all MBL null mice had died compared with 55% survival of WT mice. In contrast, i.p. inoculation of $S.$ $aureus$ did not result in enhanced infectious complications in MBL null mice compared with WT mice unless mice were rendered neutropenic but not neutropenic WT mice. The neutropenic MBL null mice displayed enhanced bacterial accumulation in organs and had persistent bacteremia 10 days post inoculation. Our results are consistent with a proposed role for MBL in first line host defense. Accordingly, the KO mice of the invention provide an ideal in vivo model system to study resistance to microbial infections and immunomodulation in the absence of the MBL complement pathway.

Surprisingly, it has also been discovered that the response of MBL KO mice of the invention to antigenic stimulation is robust and rapid. Accordingly, the KO mice can be used to advantage for the production of monoclonal antibodies to a variety of different antigens including those having binding affinity for peptides and polysaccharides.

While KO mice are described herein, the alterations to the MBL gene(s) can include modifications, deletions, and substitutions. Modifications and deletions render the naturally occurring gene nonfunctional, producing a "knock out" animal. Substitutions of the naturally occurring gene for a gene from a second species results in an animal which produces an MBL gene from the second species. Substitution of the naturally occurring gene for a gene having a mutation results in an animal with a mutated MBL protein. A transgenic mouse carrying the human MBL gene is generated by direct replacement of the mouse MBL gene with the human gene. These transgenic animals are critical for drug antagonist studies on animal models for human diseases and for eventual treatment of disorders or diseases associated with cellular activities modulated by MBL. A transgenic animal carrying a "knock out" of MBL is useful for the establishment of a nonhuman model for diseases involving MBL regulation.

As a means to define the role that MBLs play in mammalian systems, mice have been generated that cannot make MBL because of a targeted mutational disruption of the MBL-A and MBL-C genes. These mice develop normally and were healthy, viable, and fertile.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered MBL gene generally should not fully encode the same MBL protein native to the host animal and its expression product should be altered to a minor or great degree, or absent altogether. However, it is conceivable that a more modestly modified MBL gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated MBL genes to selectively inactivate the wild-type gene in totipotent ES cells (such as those described above) and then generate transgenic mice. The use of gene-targeted ES cells in the generation of gene-targeted transgenic mice was described, and is reviewed elsewhere.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the fraction of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Such mice may be used to advantage to identify agents which augment, inhibit or modify the activities of MBL. For example, MBL knock out mice are highly susceptible to i.v. inoculation with *S. aureus* when compared to inoculation of wild-type animals. Accordingly, therapeutic agents for the treatment or prevention of microbial infections may be screened in studies using MBL knock out mice. For example, MBL knockout mice may be inoculated with a particular microbe, including but not limited to bacteria, a virus, a fungus, or a parasite and treated with a test compound useful for the treatment of invention. Secondary reagents could also be assessed which compensate for the MBL deficiency. Such assays will not only facilitate the identification of agents useful for the treatment of infection, they should also be illustrative of the underlying molecular mechanisms by which MBL acts to influence the immune response.

MBL knockout mice respond to antigenic stimulation in a rapid and robust fashion. Thus, in another embodiment of the invention, MBL deficient mice are exposed to an antigen of choice for a suitable time period and spleens from such animals are used in fusions for the creation of hybrid cell lines which produce monoclonal antibodies. Advantageously, the titer of antibodies rises quickly in the KO mice of the invention, enabling the skilled person to harvest the spleens for fusion more rapidly than when conventional, wild-type mice are used.

The following examples are provided to illustrate certain embodiments of the invention. They are not intended to limit the invention in any way.

EXAMPLE I

The following methods are provided to facilitate the practice of Example I.

Generation of MBL Null Mice.

A genomic DNA clone encoding MBL-C was isolated from a 129SvJ library in Lambda Fix II vector (Stratagene, La Jolla, Calif.) and mapped (54). The MBL-C gene was disrupted by introducing the neomycin resistance gene (neor) into exon 6. The MBL-C gene targeting construct consists of a 4.5 kb PmeI-NotI fragment towards the 5' end followed by neor, then a 1.5 kb PacI-SrfI fragment towards the 3' end in a KO3 vector (FIG. 1a) (a gift from Dr. K Moore, Lipid Metabolism Unit at the Massachusetts General Hospital). Seventeen out of 111 embryonic stem cell (ES) clones underwent homologous recombination. This was confirmed by Southern blot analysis (data not shown).

The positive ES clones were injected into C57Bl/6J blastocysts at the Transgenic and Knockout Mouse Core Facility at the Massachusetts General Hospital, Boston, directed by Dr. En Li. Genotyping was done by PCR (supplemental information FIG. 1). A colony of MBL-C KO mice was expanded and some were crossed with MBL-A KO (48) mice to create MBL null mice. All animal experiments were carried out under a protocol approved by the Subcommittee on Research Animal Care at Massachusetts General Hospital.

Reverse Transcriptase-PCR(RT-PCR).

RT-PCR was described previously (48).

Detection and Assay of MBLs.

The assay for MBL was previously described (46) Complement component 4 (C4) cleaving activity of purified MBLs and rhMBL was measured by previously reported methods (55) with modification.

Briefly, microtiter wells were coated with mannan and a diluted mixture of different amounts of MBLs in 2.5% MBL null mouse serum was added to the wells. After incubation at 37° C. and rinsing, deposited C4 fragments were detected with biotinylated monoclonal anti-mouse C4 followed by europium labeled streptavidin and measurement by time-resolved fluorometry. C4 converting activity in mouse serum was measured for the MBL complement pathway and the classical pathway by a modification of above methods using microtiter wells that were coated with mannan or human IgG, respectively. Diluted serum samples were added to the wells at 4° C. to avoid complement activation. After incubation at 4° C. and rinsing, human C4 was added and incubated at 37° C. The wells were rinsed and deposited C4 fragments were detected with biotinylated rabbit anti-human C4c antibody followed by alkaline phosphatase-conjugated biotin/avidin complex and p-nitrophenyl phosphate substrate and OD 415 nm was measured. S. aureus infection. All mice were between 6 and 12 weeks old, from generations F4-F11, and were maintained on a mixed background of 129SvxC57B/6J. Age and gender-matched mice were used in each experiment. The strains of S. aureus used were Reynolds capsular serotype 5 (S. aureus CP5), a gift from Dr. Jean C. Lee (Channing Laboratory, Brigham and Women's Hospital, Harvard Medical School, Boston)(56, 57) and bioluminescent S. aureus Xen 8.1 (biolumi-S. aureus), a gift from Kevin P. Francis (Xenogen Corp., Alameda, Calif.) that is a modification of S. aureus 8325-4 (58). The biolumi-S. aureus was used for studies of in vivo imaging whereas the rest of the studies were performed with the S. aureus CP5. S. aureus was grown overnight in Columbia media with 2% NaCl, washed once and re-suspended in saline. Mice were inoculated intravenously (i.v.) in the tail vein with $5\times10^6$, $5\times10^7$ or $5\times10^8$ CFU/0.2 ml saline/mouse, evaluated for complications of infection, and $5\times10^7$ CFU/mouse was chosen as the optimal dose. Dose response for intraperitoneal (i.p.) inoculation was performed with $4\times10^5$, $4\times10^6$, and $4\times10^7$ CFU/0.5 ml saline/mouse, and $2\times10^6$ CFU/mouse was the optimal dose. Neutropenia was induced by i.p. injection of cyclophosphamide (CY) at 150 mg/kg and 100 mg/kg at 4 and 1 days prior to S. aureus inoculation, respectively.

For reconstitution experiments, 75 μg of rhMBL (a gift from NatImmune A/S, Copenhagen, Denmark) in 0.2 ml saline/mouse was injected i.p. 1 h prior to the inoculation and then daily for 3 days following inoculation since a half-life of rhMBL via i.p. injection was 14-20 hours (unpublished observation). Serum levels of rhMBL measured at one day after injection ranged between 5 and 11 μg/ml which is in the physiological range in mouse.

In Vivo Bioluminescence Imaging.

The low light imaging system (Hamamatsu Photonics KK Bridgewater, N.J.) has been previously described in detail (59). Bacterial load in blood and organs. Blood was collected from the tail vein and immediately mixed with heparin. Organs were harvested from euthanized mice, weighed and homogenized in saline (2 ml for liver and 1 ml for the other organs). Serial dilutions of the blood and the organ homogenates were cultured on tryptic soy agar plates supplemented with 5% sheep blood plates (TSA-II) overnight at 37° C. CFUs were calculated as CFU/ml for blood and CFU/g of wet weight for organs.

Bacterial Growth Assay in Plasma, Serum and Whole Blood.

Plasma and serum were collected from hirudin treated blood and coagulated blood at room temperature for 2 h, respectively. Serum, plasma or hirudin treated blood (60 μl) was mixed with S. aureus CP5 ($1\times10^5$ CFU/ml) in a 100 μl reaction volume. After the mixtures were cultured at 37o C for 2 h, 10 μl samples were removed, diluted and plated on TSA-II plate. CFUs were determined after overnight culture. Cytokine assay. TNF-α and IL-6 were measured by ELISA kits (R&D System, Minneapolis, Minn.) according to the manufacturer's instructions as described previously (48).

Phagocytosis Assays.

Resident peritoneal macrophages were obtained by peritoneal lavage. FITC-labeled S. aureus CP5 (FITC-S. aureus) were opsonized in 40% serum (v/v in HBSS) at 37° C. for 30 minutes, washed and suspended in 100 μl HBSS to a concentration of $2.5\times10^8$ cells/ml. Macrophages ($1.25\times10^5$) were mixed with $1.25\times10^7$ opsonized FITC-S. aureus in 100 μl HBSS and incubated at 37° C. for 30 minutes. The extracellular fluorescence was quenched by the addition of 200 μl PBS containing 0.04% trypan blue and 1% formaldehyde (pH 5.5) and ingested bacteria were scored by flow cytometry (60). Triplicate experiments were repeated twice. For in vivo phagocytosis assay, $2\times10^7$ FITC-S. aureus were inoculated i.p. and 10 minutes thereafter peritoneal cells were collected individually by peritoneal lavage and washed once before quenching. Flow cytometry assays were performed on a BD FACS Calibur System (BD Biosciences, San Jose, Calif.). Results were analyzed using CellQuest software.

Statistical Analysis.

Data of abscess formation was assessed by ÷2-test (JMP5 software, SAS institute, Cary, N.C.). Data of bacterial loads was analyzed by ANOVA using Statview (SAS institute, Cary, N.C.).

Generation and Characterization of MBL Null Mice

MBL null mice were generated by crossing MBL-A KO and MBL-C KO mice. MBL-C KO mice were created by introducing neor gene into exon 5 (FIG. 1a). MBL-A KO mice were generated as described previously (48). Disruption of the MBL genes was confirmed by the lack of mRNA for MBLs in the liver, the principle site of MBL synthesis (49), and undetectable MBLs in serum (FIGS. 1b and c). MBL-A KO, MBL-C KO and MBL null mice were healthy, viable, fertile, and appeared normal with no obvious developmental defects (results not shown).

Histological examination of lung, liver, spleen, lymph node, kidney, brain and intestine derived from mice 6-10 weeks old did not reveal any obvious abnormality (results not shown).

We next examined the MBL complement pathway in both MBL-C KO and MBL null mice. This third novel pathway of complement activation requires that MBL engages a ligand to trigger the activation of MASPs that generate the C3 convertase, C4bC2b (22, 23). The MBL dependent deposition of C4b is therefore an accurate measurement of this pathway. Previously we reported that serum levels of MBL-C in MBL-A KO mice were similar to levels in WT mice and that the MBL complement pathway in these MBL-A KO mice was half that of WT mice (48). These results suggested that both MBL-A and MBL-C contributed to this pathway in mice. MBL-C KO mice had slightly elevated serum levels of MBL-A compared to WT mice (FIG. 1c). This result is likely explained by the fact that MBL-A is an acute phase reactant. However as was observed in MBL-A KO mice, the MBL complement pathway was reduced by 50% in MBL-C mice (FIG. 1d).

To investigate the relative complement activating ability of MBL-A and MBL-C we performed a dose response using purified MBL-C and MBL-A (43) that were added back to MBL null mouse serum and subsequently measured MBL dependent C4 deposition. The specific activity of MBL-A was approximately 4 times that of MBL-C (FIG. 1e). However, the serum levels of MBL-C were 3 fold those of MBL-A in WT mice (FIG. 1c). Taken together, these results indicate MBL-A and MBL-C have equivalent total activity in serum. Importantly and relevant to later reconstitution experiments, rhMBL was active in mouse serum in vitro and that its specific activity was equal to that of mouse MBL-A and four times that of MBL-C (FIG. 1e). This suggests that in so far as complement activation is concerned MBL-A and MBL-C are redundant. As expected the MBL complement pathway was not functional in MBL null mice, as neither MBL-A nor MBL-C is found in the serum (FIG. 1d, left panel). As shown in FIG. 1d the classical pathway was unaffected in MBL null mice.

MBL Null Mice are Highly Susceptible to S. aureus Bacteremia.

Resistance against S. aureus is multi-factorial. The products of neutrophils and platelets, complement and peptidoglycan recognition proteins like Toll-like receptor 2 are key components in the initial armamentarium against this pathogen (61, 62). Furthermore, it has recently been shown in vitro that complement dependent killing of S. aureus is mediated via the MBL complement pathway rather than the classical or the alternative complement pathways (25).

Figure 2:
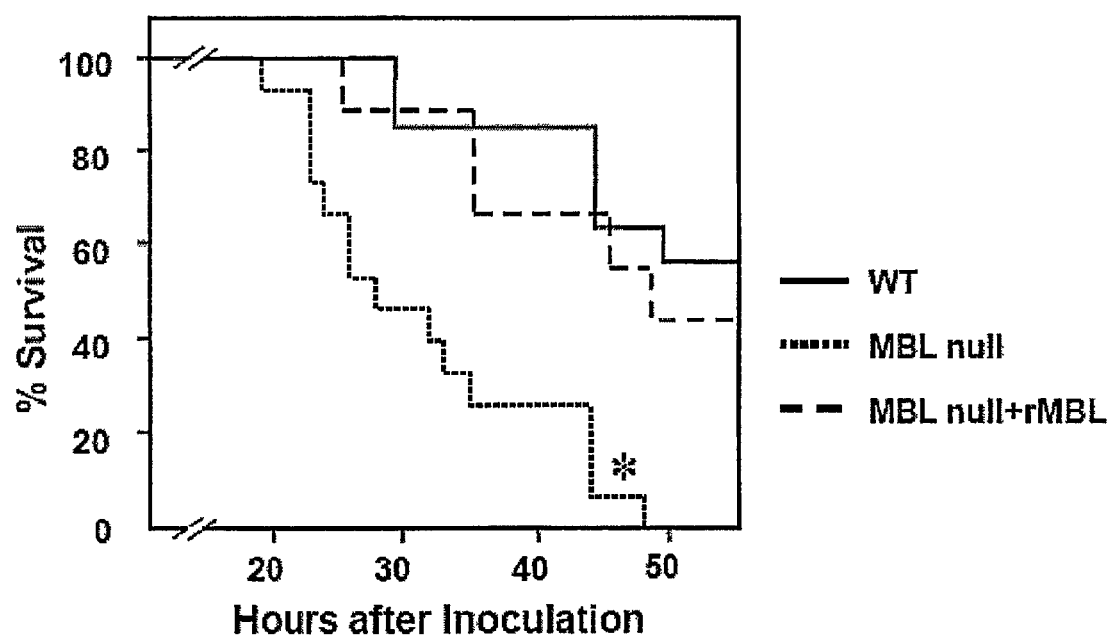
FIG. 2. Increased mortality in MBL null mice from $S.$ $aureus$ infection. $S.$ $aureus$ was inoculated i.v. and survival was followed as described in the Materials and Methods. Numbers of mice used were 15 WT, 14 MBL null and 9 MBL null+rhMBL. *, p<0.0001.

To evaluate the in vivo role of MBL against infection with S. aureus, WT and MBL null mice were inoculated i.v. with $5 \times 10^7$ CFU of S. aureus/mouse and survival was monitored. At 48 h the mortality was 100% for MBL null mice compared with 55% survival for WT mice (FIG. 2). Furthermore pretreatment of MBL null mice with rhMBL partially rescued the phenotype in that the survival of MBL null mice was 45% by 48 h (FIG. 2). The phenotype of MBL-A KO and MBL-C KO mice was similar to that of WT mice (unpublished observation). These results suggest that these two forms of MBL play a redundant role in resistance to S. aureus infection and that only when both proteins are absent the susceptibility to S. aureus is revealed.

Figure 3:
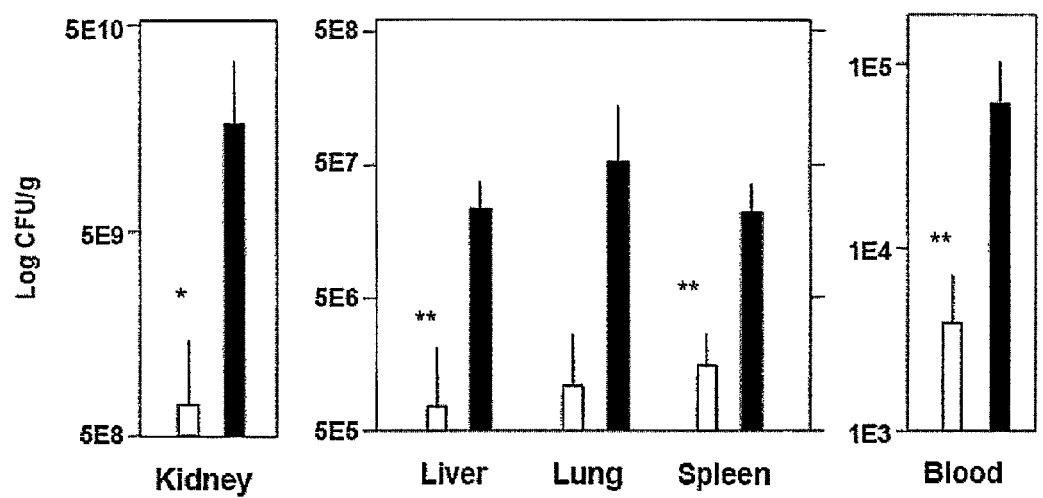
FIG. 3. Increased bacterial loads in blood and organs of MBL null mice. Bacterial titers were assayed at 24 h after i.v. inoculation of $S.$ $aureus$ as described in the Materials and Methods. Six mice were in each group. WT, open bars; MBL null, filled bars. Bars indicate mean ±SD. *, p 0.05; **, p<0.01.

We next investigated whether the enhanced susceptibility of MBL null mice to S. aureus infection was a result of altered distribution and growth of the bacteria in the blood, kidney, spleen, liver and lung. One and half logs more CFU/ml was found in the blood of MBL null mice compared with WT mice at 24 h post inoculation (FIG. 3). It was not possible to examine the later kinetics of bacteremia in MBL null mice as all had died by 48 h, but longer studies in WT mice that survived the infection indicated that these mice sterilize the blood several days after inoculation (results not shown). There were statistically significant higher bacterial loads in the kidney, spleen and liver in MBL null mice compared with WT mice 24 h post inoculation (FIG. 3).

In order to evaluate the relative contribution of direct complement mediated lysis and MBL dependent opsonophagocytosis, we incubated S. aureus in plasma and serum of WT, MBL null and C3 null mice. We found that none of the plasma (FIG. 4a) and sera (data not shown) restricted the growth of bacteria at 10 minutes or 2 h post inoculation. Additionally there was no difference in the growth rate at all three conditions (FIG. 4a). By contrast ex vivo whole blood killing assay revealed that after 2 h incubation the growth of S. aureus was restricted in whole blood from WT mice compared to 10 minutes incubation whereas S. aureus continued to grow in whole blood from MBL null mice (FIG. 4b). These results indicate that phagocytes and MBL and complement are required for S. aureus killing.

Role of MBL in Cytokine Response to S. aureus Infection

Figure 5:
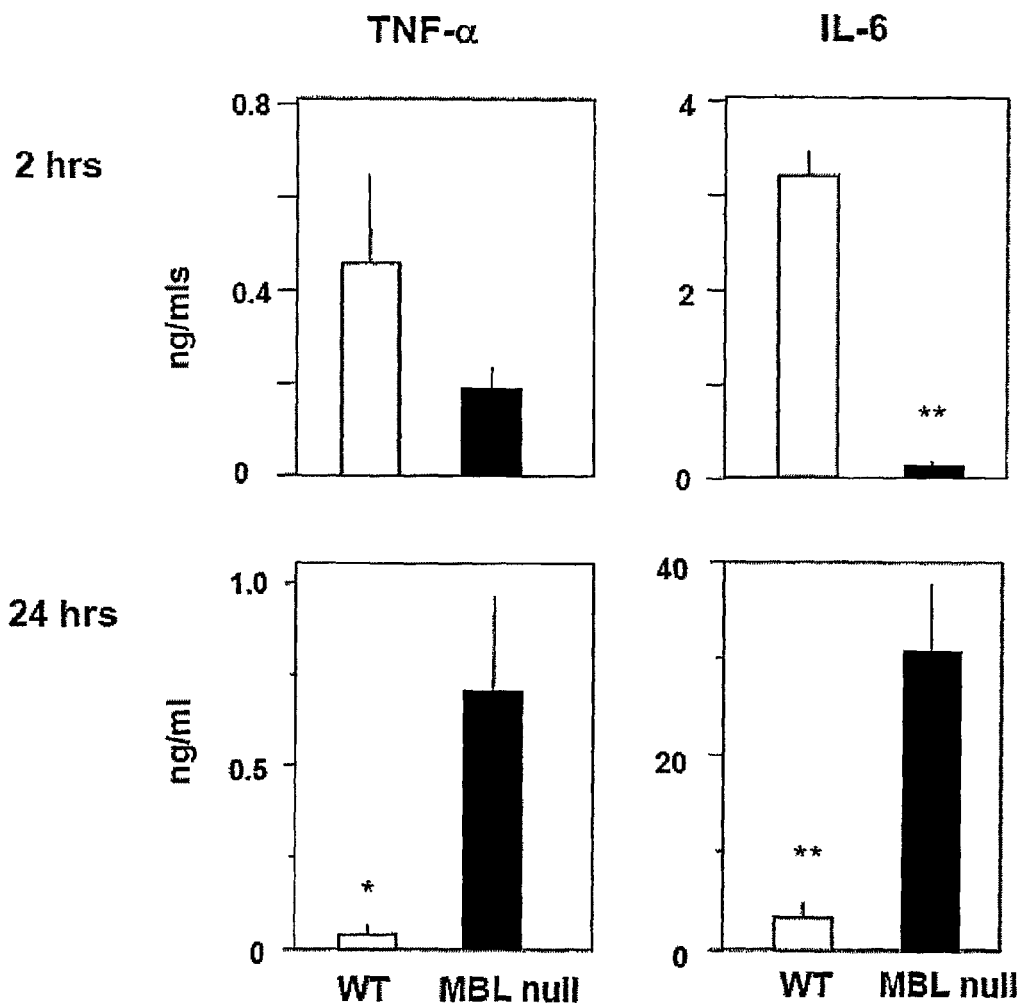
FIG. 5. Cytokine production following $S.$ $aureus$ infection. Levels of cytokine induction was less at 2 h but more at 24 h in MBL null mice compared with WT mice after $S.$ $aureus$ inoculation (i.v.). Six mice were used in each group. Bars indicate mean ±SE. *, p=0.05; **, p<0.01

The levels of TNF-α and IL-6 in the blood of MBL null and WT mice were determined at 2 and 24 h after the i.v. inoculation. Both TNF-a ($p<0.012$) and IL-6 ($p<0.0001$) were reduced in the serum of MBL null mice compared with WT mice at 2 h (FIG. 5). In contrast, at 24 h there was 2-3 fold increase in TNF-α ($p<0.01$) and eight fold increase in IL-6 ($p<0.0005$) in the serum of MBL null mice compared with WT mice (FIG. 5). Preliminary in vitro studies with bone marrow-derived macrophages from MBL null mice that were cultured with heatkilled S. aureus showed enhancement of IL-6 secretion at 24 h. A similar trend was also observed for TNF-α secretion (data not shown).

MBL and Neutrophils are Required to Combat Intra Peritoneal Challenge of S. aureus.

The role of MBL in restricting tissue infection as it developed in the peritoneal cavity was evaluated. We adapted a modified rat infection model of S. aureus (57) to mice by administering the bacteria i.p. to achieve a slower seeding into the blood and tissues. In this way we could assess the role of MBL in combating infection in inflamed body cavities. Bacteremia and abscess formation were evaluated at various time points up to 10 days after i.p. inoculation of S. aureus ranging between $4 \times 10^5$ and $4 \times 10^7$ CFU/mouse. Even the highest dose of bacterial inoculation did not show difference in survival between WT, MBL-A KO and MBL null mice. We chose a dose of $2\times10^6$ CFU/mouse and compared abscess formation in WT, MBL-A KO and MBL null mice.

Figure 6:
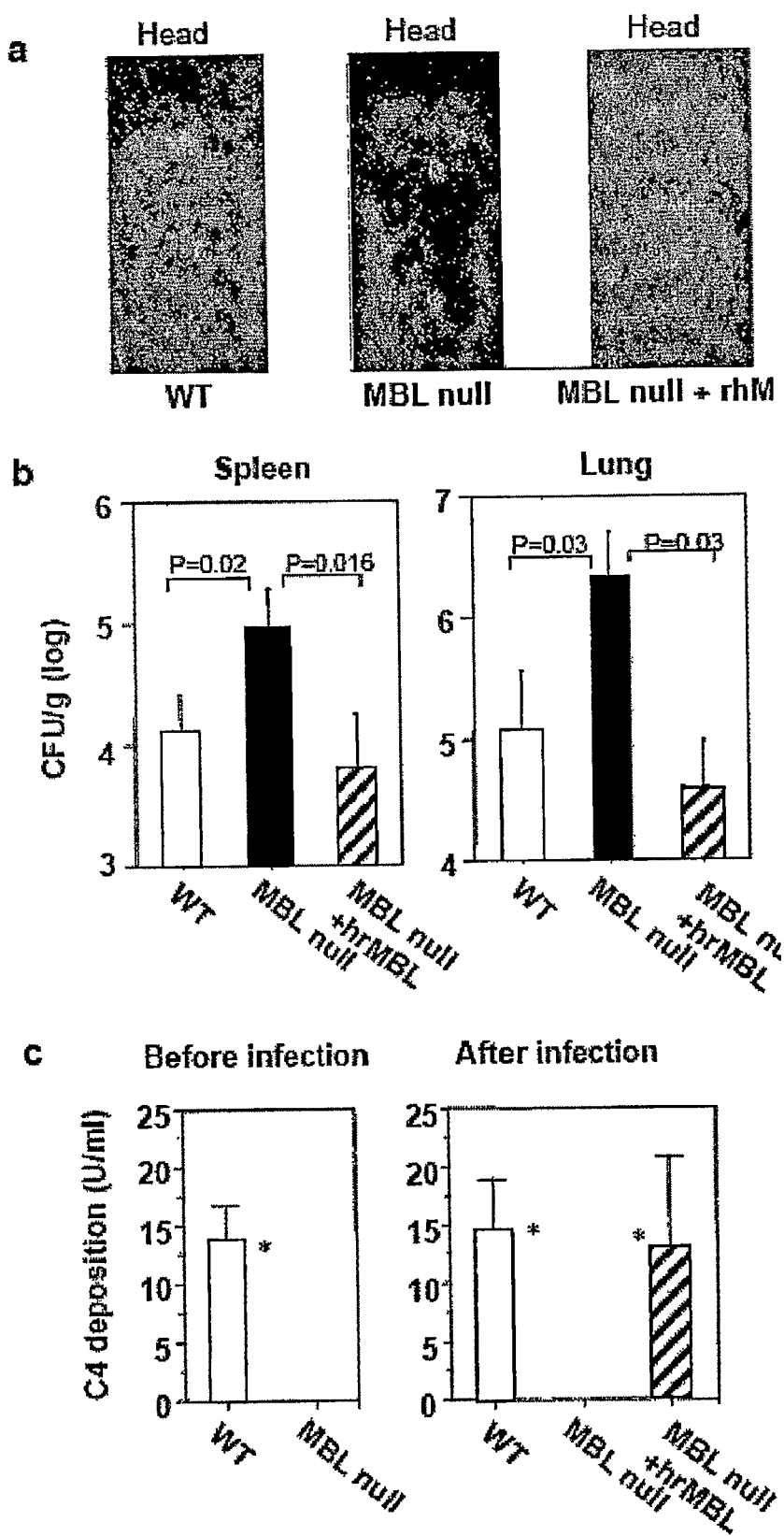
FIG. 6. Increased $S.$ $aureus$ infection in MBL null mice and rescued MBL complement pathway by rhMBL in MBL null mice. a, In vivo imaging of mice at 48 h after inoculation of the biolumi-$S.$ $aureus$ was performed as described in the Materials and Methods. Representative pictures from WT, MBL null and MBL null that were reconstituted with rhMBL (MBL null+rhMBL) are shown here. b, Increased level of bacteria in organs from MBL null mice. Organs were harvested at 96 h after the infection with biolumi-$S.$ $Aureus$ and bacterial load was measured as described in the Materials and Methods. Bars indicate mean ±SD. Numbers of mice used: WT, 8; MBL null, 7; MBL null+rhMBL, 7. c, MBL complement pathway activity before and after $S.$ $aureus$ CP5 infection. Plasma was collected at 4 days before as a base line and 4 days after $S.$ $aureus$ inoculation and analyzed for C4 deposition activity on mannan as described in the Materials and Methods. Numbers of mice used: before infection, WT, 12; MBL null, 19; after infection, WT 12; MBL null, 10; MBL null+rhMBL, 9. Two experiments were combined. Bars indicate mean ±SD. *: p 0.002.

There was no abscess formation in organs that we examined in any of the mice tested (FIG. 6). We did not test MBL-C KO mice as we assumed that they would be similar to MBL-A KO mice based on equivalence of MBL-A and MBL-C dependent complement pathway activity in the serum (FIG. 1e). Of note MBL is detectable in the peritoneal cavity of WT mice within hours of an inflammatory challenge (results not shown).

Clinical observations indicate that cancer patients with chemotherapy induced neutropenia who have MBL haplotypes that specify low serum levels of MBL have an increased incidence of infections compared with similar populations of MBL sufficient patients (38, 63, 64). We decided to simulate the clinical situation of febrile neutropenia to test this observation under controlled experimental conditions. MBL null and WT mice were rendered neutropenic by i.p. injection of CY. Four days after injection of CY all mice were neutropenic at which time these mice were inoculated with S. aureus. By 10 days post inoculation, 21 out of 29 neutropenic MBL null mice developed significant numbers of visible abscesses in organs compared with 3 out of 15 neutropenic WT mice (Table 1, p=0.0003).

The most frequent target organ in MBL null mice was the liver (17/29) followed by the kidney (12/29) and the lung (9/29), while the spleen seemed relatively resistant to later infection (2/29) (Table 1). There was no statistically significant difference between the neutropenic MBL-A KO and neutropenic MBL-C KO and neutropenic WT mice indicating that MBL-A and MBL-C are redundant under these circumstances.

TABLE 1

ABSCESS FORMATION IN ORGANS
NUMBERS OF MICE WITH ABSCESS FORMATION
PER TOTAL MICE IN EACH GROUP

|  | Kidney | Liver | Lung | Spleen | Any combination |
|---|---|---|---|---|---|
| WT + CY* | 1/15 | 3/15 | 1/15 | 0/15 | 3/15 |
| MBL-A KO + CY | 1/7 | 2/7 | 0/7 | 0/7 | 2/7 |
| MBL-C KO + CY | 0/9 | 3/9 | 0/9 | 0/9 | 3/9 |
| MBL null + CY | 12/29 (0.010)** | 17/29 (.012) | 9/29 (0.49) | 2/29 | 21/29 (0.0003) |
| WT | 0/8 | 0/8 | 0/8 | 0/8 | 0/8 |
| MBL-A KO | 0/7 | 0/7 | 0/7 | 0/7 | 0/7 |
| MBL-null | 0/9 | 0/9 | 0/9 | 0/9 | 0/9 |

*CY = Cyclophosphamide;
**Numbers in parentheses indicate P-values against WT + CY mice group.

Neutropenic MBL Null Mice Accumulate More Bacteria in Blood and Organs Compared with Neutropenic WT Mice by day 4 of Infection.

The kinetics of bacterial proliferation following infection in the peritoneal cavity was assayed. In particular we aimed to test the role of MBL in the complicated interplay between the bacteria and host. For S. aureus infection, this revolves around the ability of the host to adapt and to resist the broad array of bacterially derived pathogenicity factors. To this end, neutropenic WT and neutropenic MBL null mice were inoculated i.p. with biolumi-S. aureus and the resulting infection was followed 1 h and then daily after inoculation in real time by in vivo bioluminescence imaging. The accumulation of bacteria in the kidney and in the paratracheal lymph nodes was evident by two days in neutropenic MBL null mice compared with no accumulation in neutropenic WT mice (FIG. 6a).

For more definitive proof, bacterial titers in blood and organ were determined inborder to quantitate biolumi-S. aureus. There was no significant difference in bacterial titers in the blood until day 3 post inoculation. However, by day 4 there were two log difference between neutropenic WT mice with $1\times10^5$ CFU/ml and neutropenic MBL null mice with $2\times10^7$ CFU/ml (p=0.037). By day 8 post inoculation the neutropenic WT mice had sterilized their blood while there was persistent bacteremia in the neutropenic MBL null mice despite a recovery of circulating neutrophils (results not shown).

There were 10 to 100 fold higher number of S. aureus in the spleens and the lungs of neutropenic MBL null mice compared to neutropenic WT mice respectively (FIG. 6b). These bacterial titers in organs were consistent with the abscess formation data presented above.

The Phenotype is Reversed by Treatment of Neutropenic MBL Null Mice with rhMBL

We investigated the effect of treating neutropenic MBL null mice with rhMBL. Neutropenic MBL null mice that received rhMBL had no detectable collections of biolumi-S. aureus in their organs (FIG. 6a). Bacterial culture of organs confirmed that rhMBL treated neutropenic MBL null mice had 20 to 100 times less accumulation of bacteria in the spleens and lungs respectively compared with untreated neutropenic MBL null mice (FIG. 6b). As expected the MBL complement pathway was intact in neutropenic WT mice but not in neutropenic MBL null mice before infection (FIG. 6c, left panel).

The MBL complement pathway was restored in vivo in neutropenic MBL null mice that received rhMBL (FIG. 6c, right panel). These findings indicate that the reconstitution of the MBL complement pathway directly correlated with a decrease in bacterial accumulation in the tissues.

Decreased Bacterial Phagocytosis by Resident Peritoneal Macrophages in MBL Null Mice In this study we observed that neutropenic MBL null mice are more susceptible to i.p. infection than neutropenic WT mice. CY treated WT and MBL null mice, in addition to being neutropenic, had a 80% decrease in circulating monocytes and resident peritoneal macrophages indicating that the effects of chemotherapy did not affect neutrophils alone. We reasoned that despite the reduction in the number, resident peritoneal macrophages, together with MBL play a key role in restricting the early infection in the absence of neutrophils. We detected MBL in the peritoneal cavity of WT mice within hours of infection (results not shown). Resident peritoneal macrophages were harvested 10 minutes after inoculation of FITC-S. aureus into the peritoneal cavity of WT and MBL null mice and phagocytosis as bacterial uptake was analyzed by FACS.

Figure 7:
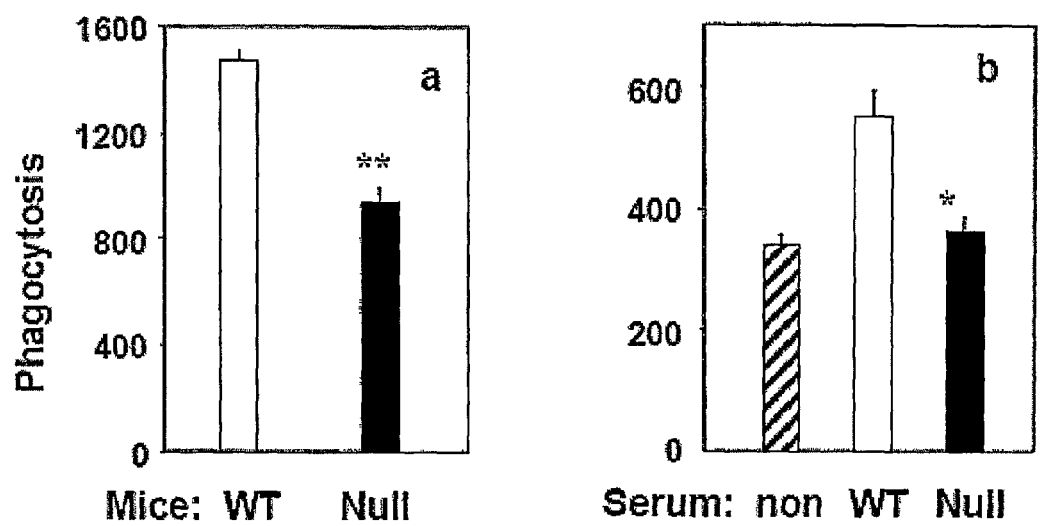
FIG. 7. Decreased macrophage phagocytosis in MBL null mice. Phagocytosis was assayed in vivo (a) and in vitro (b) as described in the Material and Methods. Phagocytosis is shown by mean fluorescence intensity for the ingested FITC-$S.$ $aureus$. Bars indicate mean ±SE. **, p=0.003; *, p=0.009.

There was a 40% reduction in bacterial phagocytosis by resident peritoneal macrophages from MBL null mice compared with those from WT mice (FIG. 7). In addition, the bacterial phagocytosis in vitro by peritoneal macrophages from WT mice was 35% less when FITC-S. aureus was opsonized with serum from MBL null mice compared with that from WT mice.

Discussion

In this study we demonstrate that mice that lack MBL-A and MBL-C (FIG. 1c) and thereby do not have a functional MBL complement pathway (FIG. 1d) are highly susceptible to infection with S. aureus. All MBL null mice succumbed by 48 h after i.v. inoculation of S. aureus (FIG. 2) and there was a corresponding 10 to 100 fold increase in S. aureus accumulation in blood, liver, spleen, kidney, and lung of MBL null mice compared to those of WT mice 24 h post inoculation (FIG. 3). The persistent bacteremia led to overwhelming sepsis and the demise of the MBL null mice. S. aureus was killed in whole blood of WT mice whereas the bacteria grew in that of MBL null mice (FIG. 4). In addition pretreatment of MBL null mice with rhMBL reversed the susceptibility phenotype.

These results suggest that MBL under the conditions of this mouse model has a non-redundant role in restricting the spread of S. aureus from the blood to the tissues. MBL and MASPs circulate in the serum as complexes (65). Once MBL recognizes a microbial surface MASP-2 co-ops the classical complement pathway convertase, which in turn leads to the deposition of the cleaved third complement component C3b (22, 23). The C3b serves as a ligand for complement receptors that are expressed on phagocytes. In addition to the enhancement of opsonophagocytosis activation of the MBL complement pathway may result in the assembly of the membrane attack complex with the resultant fluid phase lysis of the target microorganism. MBL may also directly opsonize targets for clearance by phagocytic cells that express collectin receptors. A recent study evaluated the relative importance of MBL dependent clearance mechanisms in vitro as it pertains to S. aureus (25). Importantly, that study revealed that the MBL complement pathway, but not the alternative complement pathway, was required for antibody independent C3 deposition on S. aureus. In addition it was observed that C3 opsonization of S. aureus resulted in enhanced uptake of organisms by human neutrophils. Furthermore, MBL alone in the absence of complement was also able to facilitate enhanced uptake of bacteria by phagocytic cells. We attempted to address the relative importance of these three mechanisms in defense against S. aureus. Plasma and serum from WT, MBL null mice and C3 null mice was not effective in restricting the growth of S. aureus (FIG. 4), indicating that S. aureus is resistant to direct attack via MBL, complement or the combination of MBL and complement. However, phagocytosis of S. aureus in whole blood was highly dependent of MBL (FIG. 4). Taken together, our results indicate that MBL-initiated opsonophagocytosis by both neutrophils and macrophages is an important first line host defense against S. aureus. Our studies did not address the relative role of MBL alone versus MBL mediated complement activation in mediating opsonophagocytosis.

We hope to address this point in part by creating C3 x MBL null animals. Uptake of S. aureus by phagocytes can also occur via macrophage scavenger receptors in an opsonin independent manner (66)

The net effect uptake by PMN's results in the triggering of the oxidative burst and the release of peptides and proteins like phospholipase A2 (67), cathelicidins (68), defensins (69) and cathepsin G (70) all of which can directly kill staphylococci. It would be interesting to compare MBL dependent release of these mediators with MBL independent release of these effectors as the next step in better understanding of the MBL dependent killing of S. aureus.

This study demonstrated that MBL not only acts as an opsonin but also stimulates a proinflammatory response. We noted that there was a muted cytokine response as defined by IL-6 and TNF-α levels in blood of MBL null animals at 2 h post inoculation (FIG. 5). The failure to contain the infection led to sepsis and death of the all MBL null mice by 48 h with high levels of IL-6 and TNF-α (FIG. 5) commensurate with an exaggerated host response to bacterial sepsis. These in vivo findings correlate with our in vitro findings in that S. aureus preincubated with serum from MBL null mice was relatively ineffective in triggering cytokine release via macrophages (data not shown). Based on past studies (71) we postulate that the release of appropriate amounts of TNF-α stimulate neutrophils and monocytes to possess enhanced killing activity against S. aureus as this was described in vitro study (72). We hypothesized that the relative lack of TNF-α resulted in less than optimal stimulation of neutrophils and together with the failure to activate MBL complement pathway contributed to the enhanced susceptibility of MBL null mice to infection.

We wished to evaluate the intertwining role of MBL and neutrophils further, and reasoned that local anti-staphylococci defenses would combat a low multiplicity of infection in the first instance in this body compartment. Such defense mechanisms would be supplemented during the acute inflammatory response that would include both neutrophils and MBL. Our findings that MBL null and WT mice were equally resistant to sublethal challenge of S. aureus (Table 1) demonstrate that MBL complement pathway alone is redundant in first line host defense against staphylococci in the peritoneal cavity. This is in contrast to infection in blood where MBL appears to have a non-redundant role.

The well-documented anti-staphylococcal action of platelets, phagocytic cells and their products appear sufficient to compensate for the lack of MBL. However the increased abscess formation in neutropenic MBL null mice compared with neutropenic WT mice indicates that MBL, neutrophils and resident peritoneal macrophages together provide an effective barrier to i.p. infection with S. aureus. It appears that in the absence of neutrophils and MBL the pathogen obtains a growth advantage and spreads beyond the initial infectious nidus in the peritoneal cavity to the paratracheal lymph nodes (FIG. 6a). In the neutropenic MBL null mice systemic bacterial infection ensues within days after the infectious inoculum. Organs are seeded with pathogenic bacteria and abscess formation is observed in 21/29 neutropenic MBL mice versus 3/15 neutropenic WT mice (Table 1). The restoration of MBL with exogenous MBL was required to contain the infection both locally and systemically and correlated with the restoration of the MBL complement pathway in vivo (FIG. 6c). MBL therefore fulfills the requirements that might be expected of a molecule involved in innate immunity as it is required to limit an early response to infection in the blood. Additionally, MBL is important in containing the spread of an i.p. infection, at least under the experimental conditions described in this study. Other serum opsonins, like LBP, act in concert with neutrophils and have a selective action against certain Gram negative pathogens that may be dependent on the route of infection (35). In this regard, LBP null mice are uniquely susceptible to i.p. but not per oral or i.v. infection with Salmonella typhimurium and not S. aureus (35). MBL on the other hand, binds a broader range of bacteria, fungi, certain parasites, and viruses (7).

The availability of MBL null mice will be useful in adjudicating the relative role of MBL in maintaining the balance between the host and other bacterial, viral and protozoan pathogens. The establishment of an infection reflects a balance between the virulence of the organism and susceptibility of the individual. We did not examine a wide range of S. aureus clinical isolates in this study but it is clear that S. aureus utilizes cell associated products, secreted exotoxins and regulatory loci to enhance and modify its pathogenicity. Treatment of S. aureus infections has become difficult given the emergence of widespread antibiotic resistance (52). Clinical isolates resistant to methicillin now appear to be resistant to multiple antibiotics with the recent appearance of full resistance to vancomycin (50). This raises the possibility that rhMBL may have an adjuvant role clinically together with antibiotics against antibiotic resistant staphylococci. The idea that MBL might be an infection susceptibility gene is supported by the earliest studies by Turner and colleagues (14, 15). Since that time numerous studies have indicated an association of low MBL levels with recurrent infections in both adults and children. In one study a higher proportion of patients with invasive pneumococcal disease were homozygous for MBL variant genes compared with age and race matched controls (73). The interdependence of MBL and neutrophils in combating infection also has a clinical corollary. Neth and colleagues found that children with febrile neutropenia post chemotherapy who had low secretor MBL haplotypes stayed in hospital average two days longer than those who were MBL sufficient (63). Two other studies, in adult cancer patients, demonstrated an association between low MBL levels and clinically significant events in the setting of febrile neutropenia, while one study failed to demonstrate this association (38). The increased susceptibility to infection of patients with cystic fibrosis, chronic granulomatous disease, complement deficiency, common variable immunodeficiency and antibody subclass deficiency who have low MBL secretor haplotypes provide further credence to the idea that MBL synergies with other modalities of host defense (6). Taken together these examples illustrate that MBL acts in concert with other modalities of the innate immune system to alter the balance between the host and the pathogen. Our study adds credence to this paradigm, but also indicates that if the infection is blood born, MBL has a non-redundant role, at least in the context of S. aureus bacteremia. However, for tissue infectious susceptibility required not only MBL deficiency, but also a second hit, which in this instance was neutropenia.

It would be interesting to assess the association of MBL variants and complications of S. aureus bacteremia in large cohort human studies. Given the results of this study one might predict that MBL levels might be an additional clinical identifier that is a biological marker of host resistance. Finally, our study provides direct in vivo evidence that MBL does indeed function as an "ante-antibody" in first line host defense in that the MBL together with MBL complement pathway is an important host factor that protects against the bacterial infection.

EXAMPLE II

Use of MBL Knockout Mice for the Generation of Immunospecific Monoclonal Antibodies Mannose binding lectin (MBL) binds many pathogenic organisms in vitro including Group B *Streptococcus* (GBS). MBL bound organism triggers the lectin pathway of complement activation. MBL appears to protect the host in the first minutes and hours after exposure to an infection during the lag period required to develop an adaptive immune response. Based on the data provided in the present example, it appears that MBL has a role in modulating antibody responses thus providing a link between innate and adaptive immunity. We assessed specific antibody responses to serotype III GBS (GBS III) polysaccharide (PS) alone as well as tetanus toxin (TT) conjugated GBS PS in MBL null mice. Surprisingly, MBL null mice displayed a 10 fold increase in IgG response to GBS III and GBS V PS-TT as compared to that observed in wild-type mice. This phenomenon was also observed with TT alone. These observations indicate that MBL has a profound effect on the generation of thymus dependent antibody responses.

The following methods are provided to facilitate the practice of Example II.

Mice.

All mice were female, between 6-8 weeks old, from F6-F9 generation, and were maintained on a mixed background of 129Sv×C57B/6J. MBL null mice were generated as described in Example I.

Immunization and Serum Collection.

All antigens were prepared in PBS and 0.5 ml per mouse was used. The mice were immunized intraperitoneally (i.p.) with the antigens listed in Table 2 on days 0, 21 and 41. Serum was obtained at days −5, 5, 20 and every 10 days thereafter till day 60. Serum from −day 5 served as a base line for polysaccharide specific IgG levels. Serum was collected after clotting blood at room temperature for 2 hours. Serum was stored at −80° C. freezer.

TABLE II

| Antigens | Dose (μg)/mouse |
| --- | --- |
| GBS. III$^a$ | 8 |
| GBS. III-TT | 0.8, 8 |
| GBS. V$^b$ | 8 |
| GBS. V-TT | 0.8, 8 |
| TT | 0.08, 0.8 |
| Saline | |

$^a$type III GBS;
$^b$type V GBS

ELISA.

Levels of specific antibodies against polysaccharide and TT were quantitated by ELISA, as described previously (Guttormsen et al., 1996).

As mentioned above in Example I, the mannose-binding lectin (MBL) is a serum molecule that plays a role in first line host defense. MBL binds the outer surface of infectious agents by ligating carbohydrate structures. The consequence of this interaction could either be the activation of the complement cascade via the MBL mannose-binding protein associated protease pathway or ligation of MBL receptors on the surface of lymphoid cells. It was presumed that MBL might play a role in linking the adaptive immune response with the innate immune response. In particular, we and others considered the fact that MBL would play an early role in defense against organisms within a lag period of 24 to 36 hours, the time that it takes to mount an adaptive immune response. A characteristic of the adaptive immune response might be the generation of specific antibodies against infectious agents.

Figure 9:
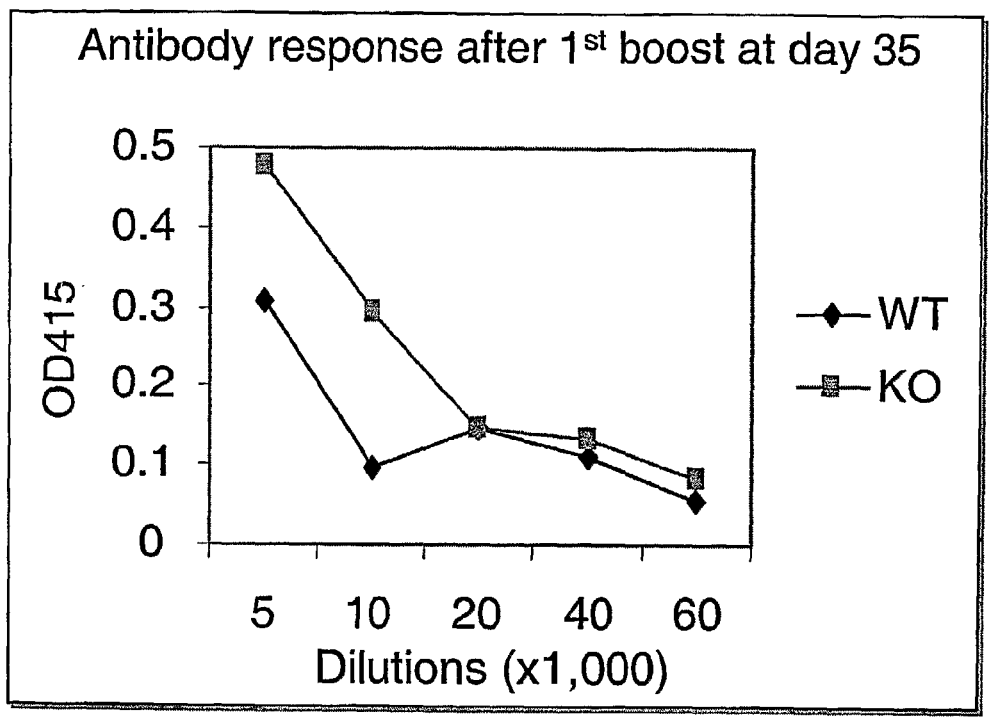
FIG. 9. A graph showing increasing titers of antibody in response to immunization with very small amounts of adenosine deaminase.

Unexpectedly, when we immunized mice that had been genetically engineered to not express either MBL-A or C genes, these mice had heightened responses firstly to polysaccharides representing the outer capsule of Group B *Streptococcus*. The responses as shown in FIG. 8 are sustained and several orders of magnitude greater than responses seen in control mice. Furthermore, we demonstrated that these responses were not restricted to carbohydrate antigens, but were also observed with peptide antigens, such as tentanus toxoid. This indicates that this enhanced response to antigen in the guise of greatly increased antibody titers is not restricted to carbohydrate antigens. The implication is that MBL plays a much more general role in modifying responses to B cell or antibody forming cell responses to all antigens. This has been confirmed by the injection of a pure protein antigen mixed with classical adjuvant Freund's adjuvant, adenosine deaminase, in which increasing titers of antibody have been observed to very small amounts of antigen. See FIG. 9.

These studies indicate that MBL null mice provide a very useful tool to develop high titer mouse antisera and high titer monoclonal antibodies to a variety of different antigens. These high level responses could be useful in generating ηg amounts of mouse monoclonal antibodies that would have applications in research, diagnostics and therapies.

Polyclonal antibodies can be generated following administration of an antigen of choice to the knockout mice of the invention, using known immunization procedures. Usually a buffered solution of the antigen accompanied by Freund's adjuvant is injected subcutaneously at multiple sites. A number of such administrations at intervals of days or weeks is usually necessary. A number of animals, for example from 3 to 20, is so treated with the expectation that only a small proportion will produce good antibodies. The antibodies are recovered from the animals after some weeks or months.

The use of monoclonal antibodies is particularly preferred because they can be produced in large quantities and the product is homogeneous. The preparation of hybridoma cell lines for monoclonal antibody production derived by fusing an "immortal" cell line and lymphocytes sensitized against the immunogenic preparation can be done by techniques which are well known to those who are skilled in the art. See, for example, Doullard, J. Y. and Hoffman, T., "Basic Facts About Hybridomas" in Compendium of Immunology, vol. II, L. Schwartz (ed.) (1981); Kohler, G. and Milstein, C., Nature, 256:495-497 (1975); Koprowski, et al., European Journal of Immunology, 6:511-519; Koprowski et al., U.S. Pat. No. 4,172,124; Koprowski et al., U.S. Pat. No. 4,196,265; and Wands, U.S. Pat. No. 4,271,145; the teachings of which are herein incorporated by reference.

Unlike preparation of polyclonal sera, the choice of animal for monoclonal antibody production is dependent on the availability of appropriate "immortal" lines capable of fusing with lymphocytes thereof. Mouse and rat have been the animal of choice in hybridoma technology and preferably used. Humans can also be utilized as sources of sensitized lymphocytes if appropriate "immortalized" cell lines are available. Surprisingly, the MBL knockout mice may be injected with less than 15 µg of antigen per mouse and still generate a robust immune response. This is in contrast to the amount of antigen used to immunize wild type mice, e.g., 0.05 mg to about 20 mg of purified antigen or fragments thereof. Usually the injecting material is emulsified in Freund's complete adjuvant. Boosting injections may also be required. The MBL mice of the invention also enable the harvesting of spleens for production of monoclonal antibody using only two injections of antigen. Additionally, use of MBL KO mice shortens the immunization period to approximately 30 days. The detection of antibody production can be carried out by testing the antisera with appropriately labeled antigen, as required by radio-immunoprecipitation, or with capture complex, as required by a variety of solid phase immunoassays including competitive ELISA. Lymphocytes can be obtained by removing the spleen or lymph nodes of sensitized animals in a sterile fashion and carrying out cell fusion. Alternatively, lymphocytes can be stimulated or immunized in vitro, as described, for example, in C. Reading, J. Immunol. Meth., 53:261-291, (1982).

A number of cell lines suitable for fusion have been developed, and the choice of any particular line for hybridization protocols is directed by any one of a number of criteria such as speed, uniformity of growth characteristics, absence of immunoglobulin production and secretion by the nonfused cell line, deficiency of metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: MPC sub 11-X45-6TG, P3-NS1-1-Ag-4-1. P3-X63-Ag8, or mutants thereof such as X63-Ag8.653, SP2-O-Ag14 (all BALB/c derived), Y3-Ag1.2.3 (rat) and U266 (human).

Cell fusion can be induced either by virus, such as Epstein-Barr or Sendai virus, or by polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000 da. The ratio between lymphocytes and malignant cells is optimized to reduce cell fusion among spleen cells and a range of from about 1:1 to about 1:10 (malignant cells:lymphocytes) gives good results.

The successfully fused cells can be separated from the myeloma line by any technique known in the art. The most common and preferred method is to choose a malignant line which is Hypoxanthine-Guanine Phosphoribosyltransferase (HGPRT) deficient, which will not grow in an aminopterin-containing medium used to allow only growth of hybrids and which is generally composed of hypoxanthine $1 \times 10^{-4}$ M, aminopterin $4 \times 10^{-7}$ M and thymidine $1.6 \times 10^{-5}$ M, commonly known as HAT medium. The fusion mixture can be grown in the HAT-containing culture medium immediately after the fusion. Cell culture usually entails maintenance in HAT medium for one week and then feeding with either regular culture medium or hypoxanthine, thymidine-containing medium.

The growing colonies are then tested for the presence of antibodies that recognize the immunizing antigen. Detection of hybridoma antibodies can be performed using an assay where the capture complex is bound to a solid support and allowed to react with hybridoma supernatants containing putative antibodies. The presence of antibodies may be detected by direct ELISA techniques using a variety of indicators. Most of the common methods are sufficiently sensitive for use in the range of antibody concentrations secreted during hybrid growth.

REFERENCES

1. Janeway, C. A. J. 1989. Approaching the Asymptote: Evolution and revolution in immunology. *Cold Spring Harbor Symp. Quanti. Biol.* 54:1-13.
2. Ezekowitz, R. A. B., and J. Hoffmann. 1998. Innate Immunity: The blossoming of innate immunity (Editorial Overview). *Curr Opin Immunol* 10:9-11.
3. Hoffmann, J. A., F. C. Kafatos, C. A. Janeway, and R. A. Ezekowitz. 1999. Phylogenetic perspectives in innate immunity. Science 284:1313-1318.
4. Tobias, P. S., and R. J. Ulevitch. 1994. Lipopolysaccharide-binding protein and CD14 in the lipopolysaccharide-dependent activation of cells. *Chest* 105:48s-50s.
5. Lu, J., C. Teh, U. Kishore, and K. B. Reid. 2002. Collectins and ficolins: sugar pattern recognition molecules of the mammalian innate immune system. *Biochim Biophys Acta* 1572:387-400.

6. Holmskov, U., S. Thiel, and J. C. Jensenius. 2003. Collections and ficolins: humoral lectins of the innate immune defense. *Annu Rev Immunol* 21:547-578.
7. Fraser, I. P., H. Koziel, and R. A. Ezekowitz. 1998. The serum mannose-binding protein and the macrophage mannose receptor are pattern recognition molecules that link innate and adaptive immunity. *Semin Immunol* 10:363-372.
8. Holmskov, U., R. Malhotra, R. B. Sim, and J. C. Jensenius. 1994. Collectins: collagenous C-type lectins of the innate immune defense system. *Immunol Today* 15:67-74.
9. Turner, M. W., and R. M. Hamvas. 2000. Mannose-binding lectin: structure, function, genetics and disease associations. *Rev Immunogenet* 2:305-322.
10. Epstein, J., Q. Eichbaum, S. Sheriff, and R. A. B. Ezekowitz. 1996. The collectins in innate immunity. *Curr Op Immunol.* 8:29-35.
11. Ikeda, K., T. Sannoh, N. Kawasaki, T. Kawasaki, and I. Yamashina. 1987. Serum lectin with known structure activates complement through the classical pathway. *J Biol Chem* 262:7451-7454.
12. Drickamer, K., M. S. Dordal, and L. Reynolds. 1986. Mannose-binding proteins isolated from rat liver contain carbohydrate-recognition domains linked to collagenous tails. Complete primary structures and homology with pulmonary surfactant apoprotein. *J Biol Chem* 261:6878-6887.
13. Kuhlman, M., K. Joiner, and R. A. Ezekowitz. 1989. The human mannose-binding protein functions as an opsonin. *J Exp Med* 169:1733-1745.
14. Super, M., S. Thiel, J. Lu, R. J. Levinsky, and M. W. Turner. 1989. Association of low levels of mannan-binding protein with a common defect of opsonisation. *Lancet* 2:1236-1239.
15. Sumiya, M., M. Super, P. Tabona, R. J. Levinsky, T. Arai, M. W. Turner, J. A. Summerfield, S. Thiel, and J. Lu. 1991. Molecular basis of opsonic defect in immunodeficient children. *Lancet* 337:1569-1570.
16. Madsen, H. O., M. L. Satz, B. Hogh, A. Svejgaard, and P. Garred. 1998. Different molecular events result in low protein levels of mannan-binding lectin in populations from southeast Africa and South America. *J Immunol* 161:3169-3175.
17. Super, M., S. D. Gillies, S. Foley, K. Sastry, J. E. Schweinle, V. J. Silverman, and R. A. Ezekowitz. 1992. Distinct and overlapping functions of allelic forms of human mannose binding protein. *Nat Genet* 2:50-55.
18. Madsen, H. O., P. Garred, S. Thiel, J. A. Kurtzhals, L. U. Lamm, L. P. Ryder, and A. Svejgaard. 1995. Interplay between promoter and structural gene variants control basal serum level of mannan-binding protein. *J Immunol* 155:3013-3020.
19. Ogden, C. A., A. deCathelineau, P. R. Hoffmann, D. Bratton, B. Ghebrehiwet, V. A. Fadok, and P. M. Henson. 2001. C1q and mannose binding lectin engagement of cell surface calreticulin and cd91 initiates macropinocytosis and uptake of apoptotic cells. *J Exp Med* 194:781-796.
20. Sheriff, S., C. Y. Chang, and R. A. Ezekowitz. 1994. Human mannose-binding protein carbohydrate recognition domain trimerizes through a triple alpha-helical coiled-coil [published erratum appears in Nat Struct Biol 1996 January; 3(1):103. *Nat Struct Biol* 1:789-794.
21. Weis, W. I., M. E. Taylor, and K. Drickamer. 1998. The C-type lectin superfamily in the immune system. *Immunol Rev* 163:19-34.
22. Matsushita, M., and T. Fujita. 1992. Activation of the classical complement pathway by mannose-binding protein in association with a novel C1s-like serine protease. *J Exp Med* 176:1497-1502.
23. Thiel, S., T. Vorup-Jensen, C. M. Stover, W. Schwaeble, S. B. Laursen, K. Poulsen, A. C. Willis, P. Eggleton, S. Hansen, U. Holmskov, K. B. Reid, and J. C. Jensenius. 1997. A second serine protease associated with mannan-binding lectin that activates complement. *Nature* 386:506-510.
24. Kuzu, I., R. Bircknell, A. L. Harris, M. Jones, K. C. Gatter, and D. Y. Mason. 1992. Heterogeneity of vascular endothelial cells with relevance to diagnosis of vascular tumors. *J Clinic Pathol* 45:143-148.
25. Neth, O., D. L. Jack, M. Johnson, N. J. Klein, and M. W. Turner. 2002. Enhancement of Complement Activation and Opsonophagocytosis by Complexes of Mannose-Binding Lectin with Mannose-Binding Lectin-Associated Serine Protease After Binding to *Staphylococcus aureus*. *J Immunol* 169:4430-4436.
26. Super, M., R. J. Levinsky, M. W. Turner, S. Thiel, and J. Lu. 1990. Association of low levels of mannan-binding protein with a common defect of opsonisation. *Clin Exp Immunol* 79:144-150.
27. Matsukawa, A., C. M. Hogaboam, N. W. Lukacs, P. M. Lincoln, H. L. Evanoff, and S. L. Kunkel. 2000. Pivotal role of the CC chemokine, macrophage-derived chemokine, in the innate immune response. *J Immunol* 164:5362-5368.
28. Chinnaiyan, A. M., M. Huber-Lang, C. Kumar-Sinha, T. R. Barrette, S. Shankar-Sinha, V. J. Sarma, V. A. Padgaonkar, and P. A. Ward. 2001. Molecular signatures of sepsis: multiorgan gene expression profiles of systemic inflammation. *Am J Pathol* 159:1199-1209.
29. Holmskov, U. L. 2000. Collectins and collectin receptors in innate immunity. *APMIS Suppl* 100:1-59.
30. Wright, J. R. 1997. Immunomodulatory functions of surfactant. *Physiol Rev* 77:931-962.
31. Wright, S. D., R. A. Ramons, P. S. Tobias, R. J. Ulevitch, and J. C. Mathison. 1990. CD14 serves as the cellular receptor for complexes of lipopolysaccharide with lipopolysaccharide binding protein. *Science* 249:1431-1433.
32. Wright, A. E., and S. R. Douglas. 1904. Opsonins. *Proc Roy Soc Ser* 73:128-142.
33. Silverstein, A. M. 2003. Cellular versus humoral immunology: a century-long dispute. *Nat Immunol* 4:425-428.
34. Yang, K.K., B. G. Dorner, U. Merkel, B. Ryffel, C. Schutt, D. Golenbock, M. W. Freeman, R. S. Jack, J. Fierer, M. A. Swancutt, and D. Heumann. 2002. Neutrophil influx in response to a peritoneal infection with *Salmonella* is delayed in lipopolysaccharide-binding protein or CD14-deficient mice. *J Immunol* 169:4475-4480.
35. Fierer, J., M. A. Swancutt, D. Heumann, and D. Golenbock. 2002. The role of lipopolysaccharide binding protein in resistance to *Salmonella* infections in mice. *J Immunol* 168:6396-6403.
36. Garred, P., H. O. Madsen, J. A. Kurtzhals, L. U. Lamm, S. Thiel, A. S. Hey, and A. Svejgaard. 1992. Diallelic polymorphism may explain variations of the blood concentration of mannan-binding protein in Eskimos, but not in black Africans. *Eur J Immunogenet* 19:403-412.
37. Summerfield, J. A., M. Sumiya, M. Levin, and M. W. Turner. 1997. Mannosebinding protein gene mutations are associated with childhood infection in a consecutive hospital series. *Br Med J* 314:1229-1232.

38. Peterslund, N. A., C. Koch, J. C. Jensenius, and S. Thiel. 2001. Association between deficiency of mannose-binding lectin and severe infections after chemotherapy. *Lancet* 358:637-638.
39. Turner, M. W. 1998. Mannose-binding lectin (MBL) in health and disease. *Immunobiol* 199:327-339.
40. Ezekowitz, R. A. B. 1991. Ante-antibody immunity. *Curr Biol* 1:60-62.
41. Mogues, T., T. Ota, A. I. Tauber, and K. N. Sastry. 1996. Characterization of two mannose-binding protein cDNAs from rhesus monkey (*Macaca mulatta*): structure and evolutionary implications. *Glycobiol* 6:543-540.
42. Laursen, S. B., T. S. Dalgaard, S. Thiel, B. L. Lim, T. V. Jensen, H. R. Juul-Madsen, A. Takahashi, T. Hamana, M. Kawakami, and J. C. Jensenius. 1998. Cloning and sequencing of a cDNA encoding chicken mannan-binding lectin (MBL) and comparison with mammalian analogues. *Immunol* 93:421-430.
43. Hansen, S., S. Thiel, A. Willis, U. Holmskov, and J. C. Jensenius. 2000. Purification and characterization of two mannan-binding lectins from mouse serum. *J Immunol* 164:2610-2618.
44. Lee, R. T., Y. Ichikawa, M. Fay, K. Drickamer, M. C. Shao, and Y. C. Lee. 1991. Ligand-binding characteristics of rat serum-type mannose-binding protein (MBPA). Homology of binding site architecture with mammalian and chicken hepatic lectins. *J Biol Chem* 266:4810-4815.
45. Ng, K. K., K. Drickamer, and W. I. Weis. 1996. Structural analysis of monosaccharide recognition by rat liver mannose-binding protein. *J Biol Chem* 271:663-674.
46. Liu, H., L. Jensen, S. Hansen, S. V. Petersen, K. Takahashi, A. B. Ezekowitz, F. D. Hansen, J. C. Jensenius, and S. Thiel. 2001. Characterization and quantification of mouse mannan-binding lectins (MBL-A and MBL-C) and study of acute phase responses. *Scand J Immunol* 53:489-497.
47. Lee, S. J., G. Gonzalez-Aseguinolaza, and M. C. Nussenzweig. 2002. Disseminated candidiasis and hepatic malarial infection in mannose-binding-lectin-A-deficient mice. *Mol Cell Biol* 22:8199-8203.
48. Takahashi, K., J. Gordon, H. Liu, K. Sastry, J. Epstein, M. Motwani, I. Laursen, S. Thiel, J. Jensenius, M. Carroll, and R. Ezekowitz. 2002. Lack of mannosebinding lectin-A enhances survival in a mouse model of acute septic peritonitis. *Microbes Infect* 4:773-784.
49. Uemura, K., M. Saka, T. Nakagawa, N. Kawasaki, S. Thiel, J. C. Jensenius, and T. Kawasaki. 2002. L-MBP is expressed in epithelial cells of mouse small intestine. *J Immunol* 169:6945-6950.
50. Diekema, D. J., M. A. Pfaller, R. N. Jones, F. J. Schmitz, J. Smayevsky, J. Bell, and M. Beach. 2002. Age-related trends in pathogen frequency and antimicrobial susceptibility of bloodstream isolates in North America: SENTRY Antimicrobial Surveillance Program, 1997-2000. *Int J Antimicrob Agents* 20:412-418.
51. Chang, F. Y., J. E. Peacock, Jr., D. M. Musher, P. Triplett, B. B. MacDonald, J. M. Mylotte, A. O'Donnell, M. M. Wagener, and V. L. Yu. 2003. *Staphylococcus aureus* bacteremia: recurrence and the impact of antibiotic treatment in a prospective multicenter study. *Medicine (Baltimore)* 82:333-339.
52. Melzer, M., S. J. Eykyn, W. R. Gransden, and S. Chinn. 2003. Is methicillinresistant *Staphylococcus aureus* more virulent than methicillin-susceptible *S. aureus*? A comparative cohort study of British patients with nosocomial infection and bacteremia. *Clin Infect Dis* 37:1453-1460.
53. Fowler, V. G., Jr., M. K. Olsen, G. R. Corey, C. W. Woods, C. H. Cabell, L. B. Reller, A. C. Cheng, T. Dudley, and E. Z. Oddone. 2003. Clinical identifiers of complicated *Staphylococcus aureus* bacteremia. *Arch Intern Med* 163:2066-2072.
54. Sastry, R., J. S. Wang, D. C. Brown, R. A. Ezekowitz, A. I. Tauber, and K. N. Sastry.
1995. Characterization of murine mannose-binding protein genes Mb11 and Mb12 reveals features common to other collectin genes. *Mamm Genome* 6:103-110.
55. Petersen, S. V., S. Thiel, L. Jensen, R. Steffensen, and J. C. Jensenius. 2001. An assay for the mannan-binding lectin pathway of complement activation. *J Immunol Methods* 257:107-116.
56. Lee, J. C., M. J. Betley, C. A. Hopkins, N. E. Perez, and G. B. Pier. 1987. Virulence studies, in mice, of transposon-induced mutants of *Staphylococcus aureus* differing in capsule size. *J Infect Dis* 156:741-750.
57. Lee, J. C., J. S. Park, S. E. Shepherd, V. Carey, and A. Fattom. 1997. Protective efficacy of antibodies to the *Staphylococcus aureus* type 5 capsular polysaccharide in a modified model of endocarditis in rats. *Infect Immun* 65:4146-4151.
58. Francis, K. P., D. Joh, C. Bellinger-Kawahara, M. J. Hawkinson, T. F. Purchio, and P. R. Contag. 2000. Monitoring bioluminescent *Staphylococcus aureus* infections in living mice using a novel luxABCDE construct. *Infect Immun* 68:3594-3600.
59. Hamblin, M. R., D. A. O'Donnell, N. Murthy, C. H. Contag, and T. Hasan. 2002. Rapid control of wound infections by targeted photodynamic therapy monitored by in vivo bioluminescence imaging. *Photochem Photobiol* 75:51-57.
60. Ramet, M., P. Manfruelli, A. Pearson, B. Mathey-Prevot, and R. A. Ezekowitz. 2002. Functional genomic analysis of phagocytosis and identification of a *Drosophila* receptor for *E. coli*. *Nature* 416:644-648.
61. Cunnion, K. M., H. M. Zhang, and M. M. Frank. 2003. Availability of complement bound to *Staphylococcus aureus* to interact with membrane complement receptors influences efficiency of phagocytosis. *Infect Immun* 71:656-662.
62. Molne, L., M. Verdrengh, and A. Tarkowski. 2000. Role of neutrophil leukocytes in cutaneous infection caused by *Staphylococcus aureus*. *Infect Immun* 68:6162-6167.
63. Neth, O., I. Hann, M. W. Turner, and N. J. Klein. 2001. Deficiency of mannosebinding lectin and burden of infection in children with malignancy: a prospective study. *Lancet* 358:614-618.
64. Mullighan, C. G., S. Heatley, K. Doherty, F. Szabo, A. Grigg, T. P. Hughes, A. P. Schwarer, J. Szer, B. D. Tait, L. Bik To, and P. G. Bardy. 2002. Mannose-binding lectin gene polymorphisms are associated with major infection following allogeneic hemopoietic stem cell transplantation. *Blood* 99:3524-3529.
65. Dahl, M. R., S. Thiel, M. Matsushita, T. Fujita, A. C. Willis, T. Christensen, T. Vorup-Jensen, and J. C. Jensenius. 2001. MASP-3 and its association with distinct complexes of the mannan-binding lectin complement activation pathway. *Immunity* 15:127-135.
66. Thomas, C. A., Y. Li, T. Kodama, H. Suzuki, S. C. Silverstein, and J. El Khoury. 2000. Protection from lethal gram-positive infection by macrophage scavenger receptor-dependent phagocytosis. *J Exp Med* 191:147-156.
67. Laine, V. J., D. S. Grass, and T. J. Nevalainen. 1999. Protection by group II phospholipase A2 against *Staphylococcus aureus*. *J Immunol* 162:7402-7408.

68. Midorikawa, K., K. Ouhara, H. Komatsuzawa, T. Kawai, S. Yamada, T. Fujiwara, K. Yamazaki, K. Sayama, M. A. Taubman, H. Kurihara, K. Hashimoto, and M. Sugai. 2003. *Staphylococcus aureus* susceptibility to innate antimicrobial peptides, beta-defensins and CAP18, expressed by human keratinocytes. *Infect Immun* 71:3730-3739.
69. Nakajima, Y., J. Ishibashi, F. Yukuhiro, A. Asaoka, D. Taylor, and M. Yamakawa. 2003. Antibacterial activity and mechanism of action of tick defensin against Gram-positive bacteria. *Biochim Biophys Acta* 1624:125-130.
70. Katzif, S., D. Danavall, S. Bowers, J. T. Balthazar, and W. M. Shafer. 2003. The major cold shock gene, cspA, is involved in the susceptibility of *Staphylococcus aureus* to an antimicrobial peptide of human cathepsin G. *Infect Immun* 71:4304-4312.
71. Ferrante, A., A. J. Martin, E. J. Bates, D. H. Goh, D. P. Harvey, D. Parsons, D. A. Rathjen, G. Russ, and J. M. Dayer. 1993. Killing of *Staphylococcus aureus* by tumor necrosis factor-alpha-activated neutrophils. The role of serum opsonins, integrin receptors, respiratory burst, and degranulation. *J Immunol* 151:4821-4828.
72. Bates, E. J., A. Ferrante, and L. J. Beard. 1991. Characterization of the major neutrophil-stimulating activity present in culture medium conditioned by *Staphylococcus aureus*-stimulated mononuclear leukocytes. *Immunol* 72:448-450.
73. Roy, S., K. Knox, S. Segal, D. Griffiths, C. E. Moore, K. I. Welsh, A. Smarason, N. P. Day, W. L. McPheat, D. W. Crook, and A. V. Hill. 2002. MBL genotype and risk of invasive pneumococcal disease: a case-control study. *Lancet* 359:1569-1573.
74. Guttormsen, H. K., Baker, C. J., Edwards, M. S., Paoletti, L. C. and Kasper, D. L. (1996) Quantitative determination of antibodies to type III group B streptococcal polysaccharide. *J Infect Dis* 173, 142-50.
75. Shi, L., Takahashi, K., Dundee, D., Shahroor-Karni, S., Thiel, S, Jensenius, J. C., Gad, G., Hamblin, M. R., Sastry, K. N., Ezekowitz, R. A. B. (2004) Mannose-binding lectin deficient mice are susceptible to infection with *Staphylococcus aureus*. J Exp Med in press.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A transgenic mouse whose genome comprises homozygous null mutations in each of the endogenous mannose-binding lectin A (MBL-A) and mannose-binding lectin C (MBL-C) genes, wherein said homozygous null mutations have been introduced into said mouse via homologous recombination in embryonic stem cells, wherein said mouse is devoid of MBL activity, wherein said mouse has undetectable levels of MBL-A and MBL-C in serum, wherein said mouse has increased susceptibility to infection by *Staphylococcus aureus* compared to a wild-type mouse, and wherein said mouse produces more IgG antibody to Group B *Streptococcus* (GBS) serotype III polysaccharide and to GBS serotype V polysaccharide conjugated to tetanus toxin than a wild-type mouse.

2. The transgenic mouse of claim 1, wherein said mouse is fertile and transmits said homozygous null mutations to its offspring.

3. The transgenic mouse of claim 1, wherein said homozygous null mutations have been introduced into an ancestor of said mouse at an embryonic stage following microinjection of embryonic stem cells into a mouse blastocyst.

4. The transgenic mouse of claim 1, wherein said homozygous null mutations have been introduced into an ancestor of said mouse at an embryonic stage following co-incubation of embryonic stem cells with a fertilized egg or morula.

5. The transgenic mouse of claim 1, wherein said homozygous null mutations are introduced via an insertion of a targeting DNA construct containing a neomycin cassette, into exon 6 of the endogenous MBL-C gene.

6. The transgenic mouse of claim 1, wherein said mouse produces more IgG antibody to tetanus toxin than a wild-type mouse.

7. The transgenic mouse of claim 1, wherein said mouse is devoid of messenger RNA of MBL-A and MBL-C in the liver.

\* \* \* \* \*